(12) United States Patent
Yang et al.

(10) Patent No.: US 11,447,778 B2
(45) Date of Patent: Sep. 20, 2022

(54) TNF-TARGETING APTAMERS AND USES THEREOF FOR TREATMENT OR DIAGNOSING TNF-RELATED INFLAMMATORY DISEASES

(71) Applicants: Academia Sinica, Taipei (TW); National Taiwan University, Taipei (TW)

(72) Inventors: Pan-Chyr Yang, Taipei (TW); Wei-Yun Lai, Taipei (TW); Jen-Wei Wang, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 151 days.

(21) Appl. No.: 17/049,048

(22) PCT Filed: Dec. 21, 2018

(86) PCT No.: PCT/US2018/067140
§ 371 (c)(1),
(2) Date: Oct. 20, 2020

(87) PCT Pub. No.: WO2019/203904
PCT Pub. Date: Oct. 24, 2019

(65) Prior Publication Data
US 2021/0254072 A1    Aug. 19, 2021

Related U.S. Application Data

(60) Provisional application No. 62/660,324, filed on Apr. 20, 2018.

(51) Int. Cl.
*C12N 15/115* (2010.01)
*A61K 47/60* (2017.01)
*G01N 33/53* (2006.01)

(52) U.S. Cl.
CPC ............ *C12N 15/115* (2013.01); *A61K 47/60* (2017.08); *G01N 33/5308* (2013.01); *G01N 2333/525* (2013.01)

(58) Field of Classification Search
None
See application file for complete search history.

(56) References Cited

FOREIGN PATENT DOCUMENTS

| CN | 107153119 | 9/2017 |
| JP | 2011-155913 | 8/2011 |
| WO | 2013/185241 | 12/2013 |

OTHER PUBLICATIONS

International Search Report and Written Opinion for International Application No. PCT/US2018/067140 dated May 1, 2019, 13 pages.
Yan, et al. "Isolation and Characterization of 2-amino-modified RNA Aptamers for Human TNF", Geno. Prat. Bioinfo. vol. 2, No. 1, Feb. 2004, pp. 32-42.
Zhou, et al. "Aptamers as targeted therapeutics: current potential and challenges", Nature Reviews: Drug Discovery, vol. 16, Mar. 2017, pp. 181-202.

*Primary Examiner* — Tracy Vivlemore
(74) *Attorney, Agent, or Firm* — Amin, Turocy & Watson, LLP

(57) ABSTRACT

Nucleic acid aptamers that bind to tumor necrosis factor alpha (TNF). Also provided herein are pharmaceutical compositions comprising such anti-TNF aptamers and methods for the using the same for therapeutic and diagnostic applications, for example, alleviating liver injury and monitoring presence of TNF in vivo or in vitro.

28 Claims, 24 Drawing Sheets
Specification includes a Sequence Listing.

… (1) …

TNF-TARGETING APTAMERS AND USES THEREOF FOR TREATMENT OR DIAGNOSING TNF-RELATED INFLAMMATORY DISEASES

RELATED APPLICATIONS

This application claims the benefit under 35 U.S.C. § 119(e) of U.S. provisional application No. 62/660,324, filed Apr. 20, 2018, which is incorporated by reference herein in its entirety.

BACKGROUND OF INVENTION

Tumor necrosis factor alpha (TNFα or TNF) is a cytokine involved in inflammation. It is mainly secreted from activated macrophages and other immune cells such as lymphocytes, neutrophils, and NK cells. TNF forms homotrimer in physiological condition and binds to its receptor TNFR1 or TNFR2 to trigger downstream NF-kB, MAPK, or death signaling pathways which regulates cell proliferation, differentiation, or apoptosis. TNF plays roles in nearly all types of inflammatory-related diseases and dysregulated TNF secretion causes diseases including rheumatoid arthritis, psoriasis, ankylosing spondylitis, inflammatory bowel disease, neurodegenerative diseases, liver injury and cancers.

Antibodies directed against TNF, however, can induce antibody-dependent cell-mediated cytotoxicity (ADCC) and complement-dependent cytotoxicity (CDC) against cells expressed membrane-bound TNF such as Kupffer cell and polymorphonuclear leukocytes. There are also no routine prediction markers for TNF concentration or diagnostic tools to detect TNF in vivo. Further, protein-based drugs such as antibodies require cell-based production systems, which are usually costly and have batch-to-batch variations.

It is therefore of great interest to develop non-protein-based agents for targeting and detecting TNF.

SUMMARY OF INVENTION

The present disclosure is based on the development of anti-TNFα (i.e.: anti-TNF) nucleic acid aptamers, which suppressed TNF signaling in vitro and attenuated TNF-mediated acute liver injury in vivo.

Accordingly, one aspect of the present disclosure features a nucleic acid aptamer that binds TNF and neutralizes the activity of TNF (anti-TNF aptamer). Any of the nucleic acid aptamers of the present disclosure may be up to 200 nucleotides (nts) in length. For example, an anti-TNF nucleic acid aptamer may consist of 40-100 nts.

In some embodiments, the nucleic acid aptamer comprises a nucleic acid motif having the nucleotide sequence of 5'-GCGCCACTACAGGGGAGCTGCCAT-TCGAATAGGTGGGCCGC-3' (SEQ ID NO: 1). Such an anti-TNF aptamer may comprise a nucleic acid sequence that is at least 85% (e.g., at least 90%, at least 95% or above) identical to SEQ ID NO: 1. In one example, the nucleic acid aptamer comprises the nucleic acid sequence of SEQ ID NO: 1. In another example, the nucleic acid aptamer consists of the nucleic acid sequence of SEQ ID NO: 1.

In some embodiments, the nucleic acid aptamer is conjugated to a polyethylene (PEG) moiety (e.g., a PEG moiety with a molecular weight of about 15-40 kDa).

In some embodiments, the nucleic acid aptamer is in a dimeric format containing two copies of the nucleic acid aptamer. In some embodiments, a PEG moiety links the two copies of the nucleic acid aptamer.

In some embodiments, the nucleic acid aptamer is conjugated to a detectable label.

Another aspect of the present disclosure features a pharmaceutical composition, comprising any of the anti-TNF aptamers described herein and a pharmaceutically acceptable carrier.

In yet another aspect, the present disclosure provides a method for inhibiting TNF activity in a subject, comprising administering to a subject in need thereof an effective amount of any of the nucleic acid aptamers described herein. In some embodiments, the subject may be a human patient having, suspected of having, or at risk for a disease mediated by TNF (e.g., rheumatoid arthritis, psoriasis, Crohn's disease, acute liver injury, acute lung injury (ALI), acute lung failure, systemic inflammatory response syndrome (SIRS)-related encephalopathy, acute respiratory distress syndrome, dry eye syndrome, uveitis, acute pancreatitis, acute glomerular injury, acute renal failure, ANCA-associated vasculitis, or acute encephalopathy). In some embodiments, the subject has undergone or is on a therapy involving a TNF antagonist. In some embodiment, the subject is at an acute phase of the disease.

In another aspect, the present disclosure provides a method for alleviating liver injury or promoting liver regeneration, comprising administering an effective amount of any of thenucleic acid aptamers described herein to a subject in need thereof. In some embodiments, the subject has liver injury associated with liver disease (e.g., hepatitis, liver cirrhosis, liver fibrosis, fatty liver disease, liver cancer, or acute liver injury). In some embodiments, the amount of the nucleic acid aptamer administered is sufficient in reducing the serum aspartate transaminase (AST) level, the serum alanine transaminase (ALT) level, or both in the subject. In some embodiments, the amount of the nucleic acid aptamer administered is sufficient in reducing neutrophil infiltration into liver of the subject.

In any of the methods disclosed herein, the nucleic acid aptamer can be administered to a subject in need of the treatment intratracheally. In some embodiments, the aptamer can be administered by inhalation or subcutaneous injection.

Further, the present disclosure provides a method for detecting the presence of TNF in a sample, the method comprising contacting an anti-TNF nucleic acid aptamer conjugated to a detectable label as described herein with a biological sample suspected of containing TNF and examining binding of the nucleic acid aptamer to TNF in the sample.

In another aspect, the present disclosure provides a method for monitoring tumor necrosis factor alpha (TNF) in vivo, comprising administering to a subject in need thereof an effective amount of an anti-TNF nucleic acid aptamer conjugated to a detectable label, and detecting localization of the nucleic acid aptamer based on a signal released by the detectable label. In some embodiments, the subject is a human patient having or suspected of having a liver disease. In some embodiments, detecting step is performed by measuring the level of the signal released by the detectable label at the liver of the human patient.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

FIG. 2A: structure of an exemplary aptTNF-α. FIG. 2B: a graph of the dissociation constant of aptTNF-α and human TNF-α (left panel) and a chart showing that aptTNF-α binds to both human and mouse TNF-α (n=3, right panel). FIG. 2C: a photo showing in vivo detection of the aptTNF-α signals in mice with and without ALI (n=3). FIG. 2D: a chart quantifying the aptTNF-α signals in FIG. 2C. FIG. 2E: a series of photos showing the biodistribution of IRDye® 800 CW-labeled aptTNF-α at 4 h post aptamer administration (n=3). FIG. 2F: a chart quantifying the biodistribution of IRDye® 800 CW-labeled aptTNF-α shown in FIG. 2E. FIG. 2G: a series of charts showing the LDH, AST, and ALT level in blood serum at 4 h post aptamer administration (n=5).

FIG. 3A: a schematic of an exemplary dimeric aptTNF-α-PEG. The aptTNF-α aptamer comprises two copies of SEQ ID NO: 1. FIG. 3B: a chart showing that aptTNF-α-PEG binds to mouse TNF-α (n=3). FIG. 3C: a graph showing the suppressive effects of aptTNF-α, aptTNF-α-PEG, and anti-TNF-α antibody as determined by the TNF-α/NF-kB reporter assay after 4 (top panel) and 24 h (bottom panel) post TNF-α treatment (n=3).

FIG. 4A: a chart showing the effect of aptTNF-α-PEG administered intratracheally or intravenously on the blood oxygen saturation level. FIG. 4B: a chart showing the effect of aptTNF-α-PEG administered intratracheally or intravenously on the wet lung weight normalized by body weight. FIG. 4C: a series of photos showing haematoxylin and eosin (H&E) and neutrophil staining of the lung tissues. FIG. 4D: a chart showing the effect of aptTNF-α-PEG administered intratracheally or intravenously on the lung injury score. FIG. 4E: a chart showing the effect of different concentrations of aptTNF-α-PEG administered intratracheally or intravenously on the total protein in bronchoalveolar lavage fluid (BALF). FIG. 4F: a chart showing the effect of different concentrations of aptTNF-α-PEG administered intratracheally or intravenously on the total cell numbers in BALF. FIG. 4G: a chart showing the effect of different concentrations of aptTNF-α-PEG administered intratracheally or intravenously on myeloperoxidase (MPO) activity in BALF. FIGS. 4H-4J: a series of charts showing the indicated cytokine/chemokine expression levels in lung tissues. FIGS. 4A-4J include data from different treatment groups (n=6). The treatment doses were represented as μg/kg.

FIG. 5A: a series of photographs showing that aptTNF-PEG conjugate rescued severe hepatocytes death and hemorrhage in liver tissues induced by TNF and D-GalN (H&E staining) and that aptTNF-α-PEG treatment suppressed neutrophil infiltration (neutrophil staining). FIG. 5B: a chart showing superior effect of aptTNF-α and aptTNF-α-PEG compared to NAC on reducing AST serum level induced by D-GalN and TNF. FIG. 5C: a chart showing that aptTNF and aptTNF-α-PEG treatment significantly suppressed ALT serum level induced by TNF and D-GalN in a mouse model of acute liver injury. FIGS. 5D-5F: a series of charts showing that the expression level of pro-inflammatory cytokines (IL1β, IL6), and neutrophil recruitment chemokines (CXCL2) were increased by TNF and D-GalN injection and decreased by aptTNF-α or aptTNF-α-PEG treatment. FIG. 5G: a photo showing that aptTNF-α or aptTNF-α-PEG treatment increased PCNA protein expression and promoted liver regeneration in a mouse model of acute liver injury. FIGS. 5A-5G include data from liver tissues from different treatment groups (n=6). The treatment doses were represented as μg/kg.

FIG. 9A: a series of photos showing that IRDye® 800CW-labeled aptTNF-α specifically localizes to the liver of mice with endogenous TNF-α secretion and acute liver injury induced by LPS and D-GalN and not to the liver of mice without LPS and D-GalN injection, despite excretion of aptTNF-α to the bladder in both groups. FIG. 9B: a chart showing the total flux of IRDye® 800CW-labeled aptTNF-α from the liver over time. FIG. 9C: a photo showing localization of IRDye® 800CW-labeled aptTNF-α to the kidney and liver in a mouse model of acute liver injury induced by LPS and D-GalN injection.

DETAILED DESCRIPTION OF INVENTION

Figure 1:
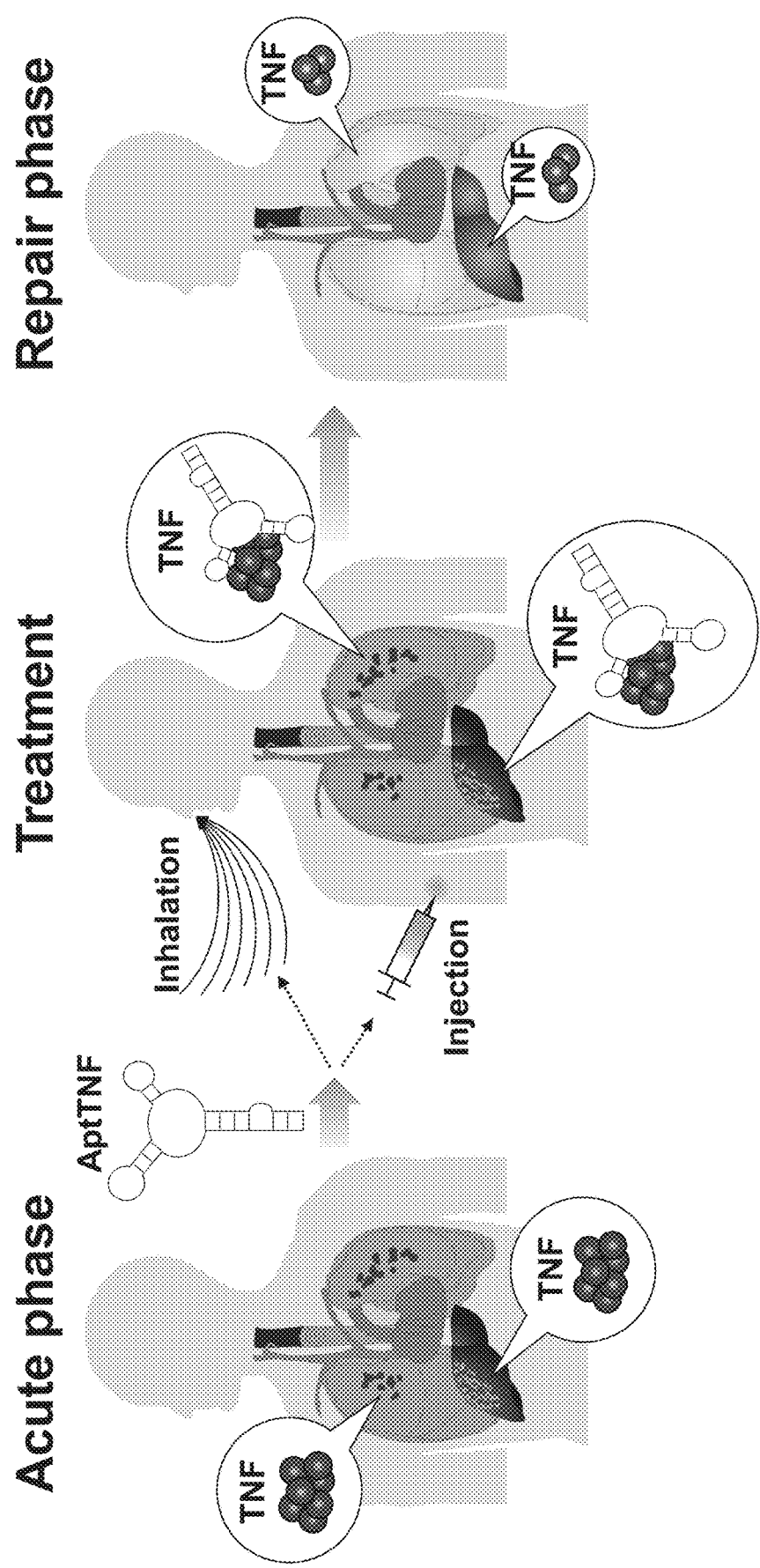
FIG. 1 is a schematic showing that aptTNF-α and/or aptTNF-α-PEG can be used to inhibit TNF-α-mediated apoptosis at the acute injury phase without affecting proliferation signaling at the tissue repair phase.

The present disclosure is based, in part, on the development of anti-TNF nucleic acid aptamers (aptTNF) and PEG conjugates thereof, which showed superior effects in inhibiting TNF signaling and attenuation of TNF-mediated acute liver injury in vivo. For example, exemplary aptamers (e.g., aptTNF or aptTNF-PEG) were found to be as effective as or better than an anti-TNF antibody in inhibiting TNF signaling in vitro. Further, results obtained from an animal model of acute liver injury showed that the exemplary anti-TNF aptamers showed similar or more effective therapeutic effects than N-acetylcysteine (a commonly used therapeutic agent for acute liver injury) in reducing levels of serum aminotransferases, which resulted in reduced neutrophil infiltration into the liver and promoted liver regeneration. Thus, anti-TNF aptamers such as those described herein would be useful in reducing inflammation, reducing liver damage, and/or promoting liver regeneration, thereby effective in treating diseases mediated by TNF, for example, liver diseases. The anti-TNF aptamers also showed tissue protective effect and systemic anti-inflammatory effect in a mouse model of acute lung injury. Further, given the binding affinity to TNF, any of the anti-TNF aptamers can also be used as diagnostic agents for detecting presence and/or level of TNF either in vitro or in vivo. Presence and/or level of TNF may serve as a biomarker in association with TNF signaling-related inflammatory disorders and cancers.

Accordingly, described herein are anti-TNF aptamers, pharmaceutical compositions comprising such, and methods of using such for therapeutic and/or diagnostic purposes.

Anti-TNF Aptamers

Described herein are nucleic acid aptamers that bind to TNF and suppresses the signaling mediated by the TNF (anti-TNF aptamers), which, as expected, would reduce inflammation. A nucleic acid aptamer as used herein refers to a nucleic acid molecule (DNA or RNA) having a binding activity for a particular target molecule (TNF such as human TNF). The aptamer can block the TNF-mediated signaling by binding to the TNF molecule. The anti-TNF aptamer of the present disclosure, in linear or circular form, may be an RNA, a DNA (e.g., a single-stranded DNA), a modified nucleic acid, or a mixture thereof. The anti-TNF aptamers may be non-naturally-occurring molecules (e.g., containing a nucleotide sequence not existing in native genes or containing modified nucleotides not existing in nature). Alternatively or in addition, the anti-TNF aptamers may not contain a nucleotide sequence that encodes a functional peptide.

TNF, referring to tumor necrosis factor (also known as tumor necrosis factor alpha, TNFα, cachexin, or cachectin), is a cytokine implicated in inflammation. It is predominantly produced by activated macrophages, but can also be produced by other cell types including neutrophils, mast cells and lymphocytes. In humans, TNF is encoded by the TNFA gene and an exemplary human TNF sequence is provided under GenBank Accession No. NP_000585.2.

The anti-TNF nucleic acid aptamer disclosed herein may comprise a nucleotide sequence at least 85% (e.g., 90%, 95%, or 98%) identical to 5'-GCGCCACTACAGGG-GAGCTGCCATTCGAATAGGTGGGCCGC-3' (SEQ ID NO: 1)

The "percent identity" of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, word-length-12 to obtain nucleotide sequences homologous to the nucleic acid molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Figure 2A:
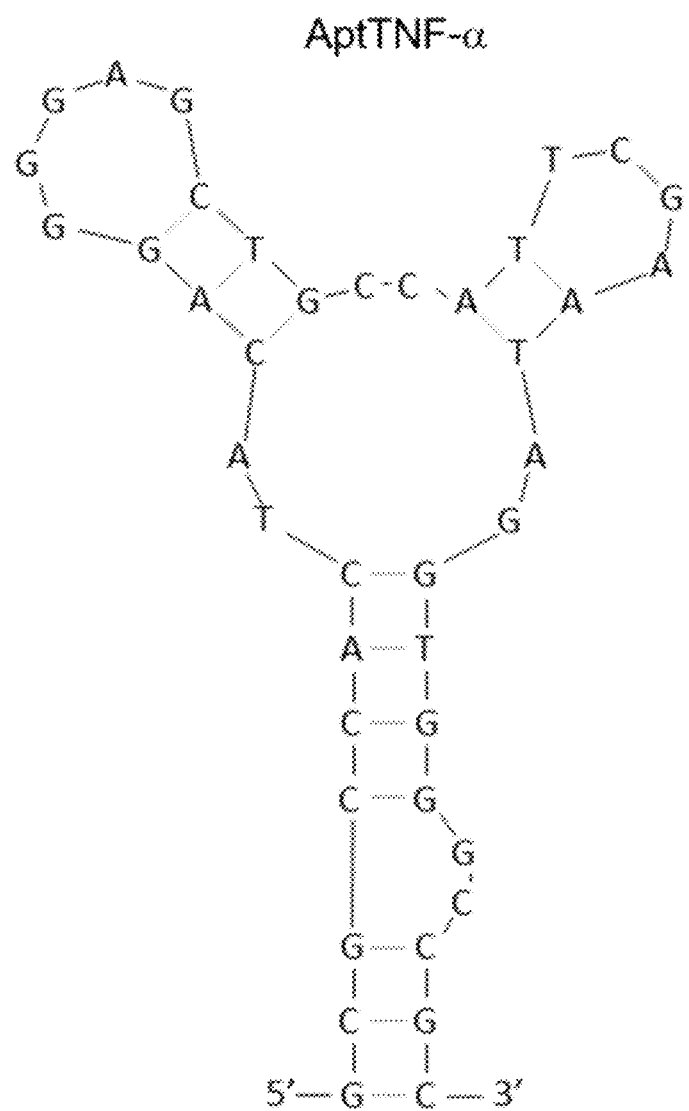
FIGS. 2A-2G include data showing that aptTNF-α binds to human TNF-α with high affinity and can serve as a molecular imaging probe for monitoring TNF-α in vivo.

In other embodiments, the anti-TNF aptamers described herein may contain up to 5 (e.g., up to 5, 4, 3, 2, or 1) nucleotide variations as compared to the nucleotide sequence of '-GCGCCACTACAGGGGAGCTGCCAT-TCGAATAGGTGGGCCGC-3' (SEQ ID NO: 1). As shown in FIG. 2A, certain parts of SEQ ID NO:1 form duplex structures. In some instances, nucleotides involved in one or more basepairs in any of the duplex segments can be switched or replaced with a different basepair. Such variants would maintain the same secondary structure as that of SEQ ID NO:1 shown in FIG. 2A and maintain all of the loop structures/sequences.

Any of the anti-TNF aptamers disclosed herein may contain up to 200 nucleotides (nts), e.g., 150 nts, 100 nts, 80 nts, 70 nts, 60 nts. 50 nts, 40 nts, or 30 nts. In some examples, the anti-TNF aptamer may contain nucleotides ranging from 30-150 nts, 30-100 nts, 30-80 nts, 30-70 nts, 30-60 nts, 30-50 nts, or 30-40 nts.

The anti-TNF aptamer may specifically bind human TNF. Alternatively, the aptamer may bind to TNF molecules from different species (e.g., human and mouse). When binding to TNF, such an aptamer may block the cell signaling mediated by TNF by at least 20% (e.g., 40%, 50%, 80%, 100%, 2-fold, 5-fold, 10-fold, 100-fold, or 1,000-fold). The inhibitory activity of an TNF aptamer on TNF-mediated signaling may be determined by routine assays and/or those described in the Examples below.

In some embodiments, the anti-TNF aptamers described herein may contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the aptamer described herein has a modified backbone, including those that retain a phosphorus atom (see, e.g., U.S. Pat. Nos. 3,687,808; 4,469,863; 5,321, 131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

In another example, the aptamers described herein include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim Acta, 1995, 78, 486-504.

Alternatively or in addition, aptamers described herein include one or more modified native nucleobases (i.e., adenine, guanine, thymine, cytosine and uracil). Modified nucleobases include those described in U.S. Pat. No. 3,687, 808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of aptamer molecules to their targeting sites. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the aptamers described herein can be prepared by conventional methods, e.g., chemical synthesis or in vitro transcription. Their intended bioactivity as described herein can be verified by, e.g., those described in the Examples below. Vectors for expressing any of the anti-TNF aptamers are also within the scope of the present disclosure.

Any of the aptamers described herein may be conjugated to one or more polyether moieties, such as polyethylene glycol (PEG) moieties, via covalent linkage, non-covalent linkage, or both. Accordingly, in some embodiments, aptamers described herein are pegylated. The disclosure is not meant to be limiting with respect to a PEG moiety of a specific molecular weight. In some embodiments, the polyethylene glycol moiety has a molecular weight ranging from 5 kDa to 100 kDa, 10 kDa to 80 kDa, 20 kDa to 70 kDa, 20 kDa to 60 kDa, 20 kDa to 50 kDa, 10 kDa to 40 kDa, 10 kDa to 30 kDa, 15 kDa to 40 kDa, 15 kDa to 30 kDa, 15 kDa to 35 kDa, 15 kDa to 25 kDa, 20 kDa to 40 kDa, 20 kDa to 35 kDa, or 20 kDa to 30 kDa. In some examples, the PEG moiety has a molecular weight of 20 kDa. The PEG moiety conjugated to the anti-TNF aptamer described herein can be linear or branched. It may be conjugated to the 5' end of the nucleic acid aptamer, the 3' end of the aptamer, or both. When needed, the PEG moiety can be conjugated to the 3' end of the nucleic acid aptamer covalently. PEG conjugation would be expected to elongate the half-life of the nucleic acid aptamer.

Methods for conjugating PEG moieties to nucleic acids are known in the art and have been described previously, for example, in PCT Publication No. WO 2009/073820 A2, the relevant teachings of which are incorporated by reference herein It should be appreciated that the PEG conjugated nucleic acid aptamers and methods for conjugating PEG to the nucleic acid aptamers described herein, are exemplary and not meant to be limiting.

In some instances, the nucleic acid aptamer may be conjugated to one or more N-acetylglycosamine (GalNAc) moieties to facilitate tissue-specific delivery (e.g., liver delivery).

Figure 3A:
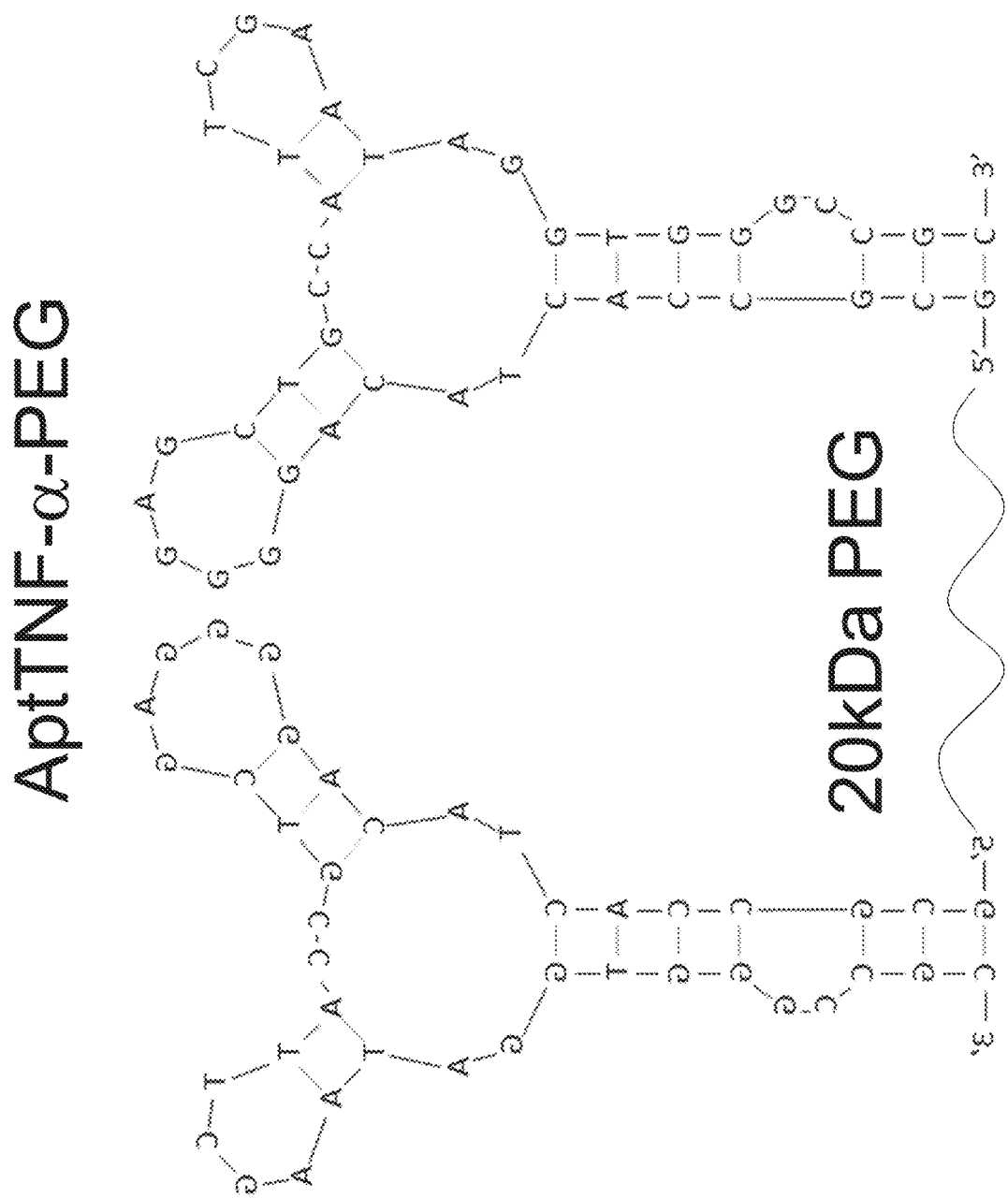
FIGS. 3A-3C include data showing that aptTNF-α-PEG has a shorter suppression duration on the TNF-α pathway than anti-TNF-α antibody.

The anti-TNF nucleic acid aptamers may be in multimeric forms, for example, in dimeric form. In some embodiments, an anti-TNF aptamer dimer may comprise two anti-TNF aptamers linked by a suitable polymer moiety, which can be a PEG moiety as those described herein. A non-limiting example of a dimeric anti-TNF aptamer is shown in FIG. 3A. Either one or both of the two aptamers in a dimer may comprise a nucleotide sequence of SEQ ID NO: 1. The two anti-TNF aptamers may be identical or different. For example, one or both of the anti-TNF aptamers may comprise SEQ ID NO: 1. In some embodiments, an anti-TNF nucleic acid aptamer is an anti-TNF aptamer dimer in which two aptamers with SEQ ID NO: 1 are connected by PEG.

Any of the anti-TNF aptamers described herein may be chemically synthesized. The aptamer may be manipulated with functional groups for conjugation with a drug for treatment purposes or a detectable label (e.g., an imaging agent such as a contrast agent) for diagnostic purposes, either in vivo or in vitro. As used herein, "conjugated" or "attached" means two entities are associated, preferably with sufficient affinity that the therapeutic/diagnostic benefit of the association between the two entities is realized. The association between the two entities can be either direct or via a linker, such as a polymer linker. Conjugated or attached can include covalent or noncovalent bonding as well as other forms of association, such as entrapment, e.g., of one entity on or within the other, or of either or both entities on or within a third entity, such as a micelle.

In one example, an anti-TNF aptamer as described herein is attached to a detectable label, which is a compound that is capable of releasing a detectable signal, either directly or indirectly, such that the aptamer can be detected, measured, and/or qualified, in vitro or in vivo. Examples of such "detectable labels" are intended to include, but are not limited to, fluorescent labels, chemiluminescent labels, colorimetric labels, enzymatic markers, radioactive isotopes, and affinity tags such as biotin. Such labels can be conjugated to the aptamer, directly or indirectly, by conventional methods.

In some embodiments, the detectable label is an agent suitable for imaging a disease mediated by TNF, which can be a radioactive molecule, a radiopharmaceutical, or an iron oxide particle. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. The reporting agent can also be a dye, e.g., a fluorophore, which is useful in detecting a disease mediated by TNF in tissue samples.

Without being bound by a particular theory, the anti-TNF aptamers described herein may confer at least the following benefits. First, the anti-TNF aptamers are small-sized molecules (e.g., having a molecular weight of about 14 kDa), which may penetrate blood-brain barrier (BBB) and be useful for treating neurodegenerative diseases. Second, manufacturing the anti-TNF aptamers does not require cell-based systems and would be cost-effective. Third, the anti-TNF aptamers would have a shorter half-life in vivo compared to protein-based therapeutic agents, such as monoclonal antibodies. As such, the anti-TNF aptamers may be more suitable for use in treating acute inflammatory diseases as they are expected to block the acute-phase TNF signaling but not affect long term innate immunity against infection.

Pharmaceutical Compositions

One or more of the anti-TNF aptamers (monomers or multimers such as dimers), or PEG conjugates thereof as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art.

See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the TNF binding aptamers (or a vector for producing the aptamer), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-TNF aptamers as described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the TNF binding aptamer, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic TNF binding aptamer compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0.im, particularly 0.1 and 0.5.im, and have a pH in the range of 5.5 to 8.0.

The emulsion compositions can be those prepared by mixing an anti-TNF aptamer with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Therapeutic and Diagnostic Applications

TNF plays roles in nearly all types of inflammatory-related diseases and dysregulated TNF secretion causes diseases such as rheumatoid arthritis, psoriasis, ankylosing spondylitis, inflammatory bowel disease, neurodegenerative diseases, acute lung injury (or acute lung failure), acute liver injury, adult respiratory distress syndrome, and cancers. As such, modulating TNF-mediated signaling and/or detecting the presence/level of TNF may be effective in treating or diagnosing TNF-mediated diseases.

Any of the anti-TNF aptamers or PEG conjugates thereof as described herein can be used for therapeutic and diagnostic uses. For example, the anti-TNF aptamers can be used to suppress TNF-mediated signaling, thereby effective in treating diseases mediated by TNF, including rheumatoid arthritis, psoriasis, Crohn's disease, asthma, systemic inflammatory response syndrome (SIRS)-related encephalopathy, liver diseases (e.g., acute liver injury), acute lung injury, acute respiratory distress syndrome, dry eye syndrome, uveitis, acute pancreatitis, acute glomerular injury, acute renal failure, ANCA-associated vasculitis, or acute encephalopathy.

Acute liver failure (ALF) or acute liver injury is a rare but life-threatening disease that in which the majority of hepatocytes undergo cell death without pre-existing liver diseases (Bernal et al., N Engl J Med. 2013; 369: 2525-34). As ALF progress, dysfunctions in other tissues including cardiovascular, respiratory, renal, central nervous, hematologic systems will soon occur. The only available treatment for ALF before liver transplantation is intravenous infusion of N-acetylcysteine (NAC) (Mumtaz et al., Hepatol Int. 2009; 3(4):563-70; Sales et al., Ann Hepatol. 2013; 12(1):6-10). However, NAC reveals no benefits to ALF patients with advanced-grade brain edema (Lee et al., Gastroenterology 2009; 137:856-64). Hence, alternative options in clinics are still unmet needs for ALF patients especially with encephalopathy and in centers without liver transplantation facility.

The underlying mechanisms behind ALF include the interplay between hepatocytes and different types of immune cells (Possamai et al., J Hepatol. 2014; 61(2):439-45). Once the hepatocytes undergo cell death, the released danger associated-molecular patterns (DAMPs) activate the resident neutrophils and hepatic macrophages (Kuppffer cells). Activated Kupffer cells will secrete tumor necrosis factor (TNF) and chemokines to recruit more monocytes and neutrophils into damaged liver tissues that aggravate death signaling in hepatocytes (Krenkel et al., 2014; 3(6):331-43; Bantel et al., Front Physiol. 2012; 3:79). Moreover, TNF will affect blood-brain barrier permeability, cause neuroinflammation, and trigger brain edema and encephalopathy (Lv et al., Liver Int. 2010; 30(8):1198-210; Bémeur et al. Neurochem Int. 2010; 56(2):213-5; Butterworth et al., Hepatology. 2011; 53(4):1372-6). Even though TNF blocking agents revealed promising therapeutic efficacy in animal models, they raised severe infections in acute alcoholic hepatitis patients (Naveau et al., Hepatology 2004; 39:1390-1397; Boetticher et al., Gastroenterology 2008; 135: 1953-1960). Severe infections might result from unwanted antibody-dependent cell-mediated cytotoxicity (ADCC) and complement-dependent cytotoxicity (CDC) effect caused by antibodies or Fc-fusion recombinant proteins which recognize the membrane-bound TNF expressed on macrophages, activated T lymphocytes and polymorphonuclear leukocytes (Naveau et al., Hepatology 2004; 39:1390-1397; Tracey et al., Pharmacol Ther. 2008; 117(2):244-79). Also, the sustained suppression of TNF/NF-κB signaling due to long half-life of these TNF blocking agents prohibits liver regeneration after acute liver injury (Naveau et al., Hepatology 2004; 39:1390-1397; Tracey et al., Pharmacol Ther. 2008; 117(2):244-79; Bhushan et al., Am J Pathol. 2014; 184(11): 3013-25).

Patients who have higher TNF concentration in serum might have better response to anti-TNF therapy and reduced side effects of infection. However, there is no routine prediction marker for TNF concentration or diagnostic tool to detect the TNF in vivo. As discussed above, the TNF-aptamers disclosed herein could be manipulated and modified to conjugate imaging agents for CT, MRI, ultrasound, and endoscopic detection (Bird-Lieberman et al., Nat Med. 2012; 18(2):315-21; Van den Brande et al., Gut. 2007; 56(4):509-17). Using aptamer to prescreen the potential responder to anti-TNF therapy may increase safety and efficacy. In some embodiments, the anti-TNF aptamers disclosed herein have theranostic effects and can be used as potential monitoring tools. The anti-TNF aptamers may serve an alternative therapeutic approach for ALF patient before liver transplantation.

Furthermore, antidote for aptTNF-α/aptTNF-α-PEG, which is the complementary sequences of the aptamer itself, can be easily designed and synthesized, which may allow for timely administration of the antidote. Without being bound by a particular theory, the anti-TNF aptamers described herein, optionally along with aptamer inhibitors (including antisense sequences), may allow for proper inhibition of the TNF-α pathway at the acute tissue injury phase, avoid suppression of regeneration at the tissue repair phase, and potentiate timely termination of the antagonistic effects whenever needed.

SIRS is a common phenomenon that occurs during end-organ damages (Bernal et al., N Engl J Med. 2013; 369: 2525-34; Ware et al., N Engl J Med. 2000; 342: 1334-49; Gattinoni et al., Am J Resp Crit Care. 2016; 194: 1051-2). As demonstrated in the ALI model described below, systemic LDH, AST and ALT levels increased and aptTNF-α signals were detected in major vital organs upon LPS-induced ALI. The surge of cytokine storm furthers a single organ disease into a systemic inflammatory disorder and can result in multiple organ dysfunctions, including central nervous, cardiovascular, respiratory, gastrointestinal, renal, and hematological system, etc. Without being bound by a particular theory, the small molecular size of the aptamers described herein may allow for efficient tissue penetration. In some embodiments, the aptamers described herein may penetrate the blood-brain barrier. Without being bound by a particular, the anti-TNF aptamers described herein may be used to treat the commonly encountered SIRS-related encephalopathy in critical care medicine.

To practice the method disclosed herein, an effective amount of the pharmaceutical composition described herein that contains at least one anti-TNF aptamer can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-TNF aptamer-containing composition as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is blockage of TNF-mediated cell signaling, reduced inflammation, reduced liver damage, and/or increased liver regeneration. Determination of whether an amount of the TNF binding aptamers achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a TNF binding aptamer may be appropriate. Various formulations and devices for achieving sustained release are known in the art.

In one example, dosages for an anti-TNF aptamer as described herein may be determined empirically in individuals who have been given one or more administration(s) of the TNF binding aptamer. Individuals are given incremental dosages of the antagonist. To assess efficacy of the antagonist, an indicator of the disease/disorder can be followed.

Generally, for administration of any of the anti-TNF aptamers described herein, an initial candidate dosage can be given to a subject in need of the treatment, which may be adjusted based on the subject's response to the anti-TNF aptamer. For the purpose of the present disclosure, a typical daily dosage might range from about any of 0.1 µg/kg to 100 mg/kg or more, depending on the factors mentioned above.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a TNF binding aptamer as described herein will depend on the specific TNF binding aptamer, the type and severity of the disease/disorder, whether the TNF binding aptamer is administered for preventive or therapeutic purposes, previous therapy, the patient's clinical history and response to the antagonist, and the discretion of the attending physician. A clinician may administer a TNF binding aptamer, until a dosage is reached that achieves the desired result. In some embodiments, the desired result is reduced inflammation (e.g., reduced neutrophil infiltration into a tissue), reduced liver damage, and/or increased liver regeneration. Methods of determining whether a dosage resulted in the desired result would be evident to one of skill in the art. Administration of one or more TNF binding aptamers can be continuous or intermittent, depending, for example, upon the recipient's physiological condition, whether the purpose of the administration is therapeutic or prophylactic, and other factors known to skilled practitioners. The administration of a TNF binding aptamer may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the TNF binding aptamers described herein are administered to a subject in need of the treatment at an amount sufficient in reducing the TNF-mediated signaling by at least 5% (e.g., 10%, 20%, 30%, 40%, 50%, 60%, 70%, 80%, 90% or greater), which can be determined via routine assays and/or those described in Examples below. In some embodiments, the TNF binding aptamers are administered in an amount effective to reduce inflammation (e.g., reduce neutrophil infiltration, reduce production of one or more proinflammatory cytokines (e.g., IL1β and IL-6), one or more macrophage recruitment chemokines (e.g., CCL2), one or more neutrophil recruitment chemokines (e.g., IL23 and IL17) or a combination thereof) in a tissue of the subject by at least 5% (e.g., 10%, 20%, 30%, 40%, 50%, 60%, 70%, 80%, 90% or greater) in vivo.

In other embodiments, the TNF binding aptamers are administered in an amount effective in reducing serum levels of aminotransferases (e.g., alanine transaminase (ALT) or aspartate transaminase (AST)) by at least 5% (e.g., 10%, 20%, 30%, 40%, 50%, 60%, 70%, 80%, 90% or greater) in a subject (e.g., in a subject with liver injury). In some embodiments, the anti-TNF aptamers are administered in an amount effective in increasing expression of cell cycle genes (e.g., cyclin D1 or PCNA) in the liver (thereby promoting liver regeneration) by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally. In some examples, the pharmaceutical composition is administered intratracheally. In other examples, the pharmaceutical composition can be administered by inhalation or by subcutaneous injection.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble TNF binding aptamers can be administered by the drip method, whereby a pharmaceutical formulation containing the TNF binding aptamer and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the TNF binding aptamer, can be dissolved and administered in a pharmaceutical excipient such as Water-for-Injection, 0.9% saline, or 5% glucose solution.

In one embodiment, a TNF binding aptamer is administered via site-specific or targeted local delivery techniques. Examples of site-specific or targeted local delivery techniques include various implantable depot sources of the TNF binding aptamer or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

In some embodiments, the aptamers described herein are compatible with different materials and can be made into different formulations for topical uses. In some embodiments, administration of an anti-TNF aptamer described herein via the intratracheal route increase allow for an optimal effect at a lower drug concentration than via the intravenous route in a subject with acute lung injury. In some embodiments, topical delivery increases local effective drug concentration and reduces systemic side effects, which may be useful in inflammatory diseases, including asthma.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., the TNF binding aptamers described herein or vectors for producing such) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The subject to be treated by the methods described herein can be a mammal, such as a farm animals, sport animals, pets, primates, horses, dogs, cats, mice and rats. In one example, the subject is a human. The anti-TNF aptamer-containing composition may be used for reducing inflammation, promoting liver regeneration, reducing liver damage, decreasing tumor burden in a subject in need of the treatment. In some examples, the subject may be a human subject having an elevated serum level of TNF as relative to a healthy human subject (e.g., free of diseases associated with TNF). Levels of TNF within a subject (e.g., in the serum of a subject) may be assessed using routine medical practices.

In some examples, the subject can be a human patient having, suspected of having or at risk for a disease mediated by TNF (including rheumatoid arthritis, psoriasis, ankylosing spondylitis, inflammatory bowel disease, acute lung injury, neurodegenerative diseases, liver injury associated with a liver disease and cancers). Exemplary liver diseases include hepatitis, liver cirrhosis, liver fibrosis, fatty liver disease and liver cancer. In some examples, the subject may be a human patient having a TNF-mediated acute inflammatory disorder. Examples include acute liver injury, acute lung injury, acute respiratory distress syndrome, dry eye syndrome, uveitis, acute pancreatitis, acute glomerular injury, acute renal failure, ANCA-associated vasculitis, acute encephalopathy.

A subject having a target disease or disorder (e.g., TNF-mediated diseases including rheumatoid arthritis, psoriasis, ankylosing spondylitis, inflammatory bowel disease, neurodegenerative diseases, acute lung injury, acute liver injury and cancers) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices. TNF levels within a subject may also be assessed using a method described herein. In some embodiments, patients with higher TNF concentration have better response to anti-TNF therapy (e.g., anti-TNF aptamer treatment) and reduced side effects caused by infection.

The particular dosage regimen, i.e., dose, timing and repetition, used in the method described herein will depend on the particular subject (e.g., a human patient) and that subject's medical history.

In some embodiments, the anti-TNF aptamer may be co-used with another suitable therapeutic agent for a target disease, such as those described herein. Alternatively or in addition, the anti-TNF aptamer may also be used in conjunction with other agents that serve to enhance and/or complement the effectiveness of the agents.

Treatment efficacy for a target disease/disorder can be assessed by, e.g., a method described in the Examples below.

In some embodiments, an anti-TNF aptamer conjugated to a detectable label (e.g., an imaging agent) as disclosed herein is administered to a subject to assess TNF levels in the subject. Such detection of TNF may be used to identify relevant patients for anti-TNF treatment (e.g., for treatment with an anti-TNF pharmaceutical composition disclosed herein or for treatment with anti-TNF antibody).

TNF may be detected in a sample (e.g., a biological sample suspected of containing TNF, including but not limited to a blood sample and urine sample) in vitro using any of the aptamers described herein via a routine method. In some instances, the aptamer may be conjugated to a detectable label, which may release a signal, directly or indirectly, indicating the presence and/or level of TNF in the sample. Alternatively, the anti-TNF aptamer may be used for in vivo imaging of presence and localization of TNF in a subject (e.g., a human patient as described herein). Results obtained from any of the diagnostic assays described herein (either in vitro or in vivo) may be indicative of a risk or state of a disease associated with TNF.

Kits for Use in Treatment or Diagnosis

The present disclosure also provides kits for use in reducing inflammation (e.g., reducing production of inflammatory proteins or reducing neutrophil infiltration), alleviating a TNF-mediated disease (e.g., rheumatoid arthritis, psoriasis, ankylosing spondylitis, inflammatory bowel disease, acute lung disease, neurodegenerative diseases, liver injury associated with a liver disease and cancers) and in detecting TNF levels in a subject. Such kits can include one or more containers comprising an aptamer that binds TNF, e.g., any of those described herein.

In some embodiments, the kit can comprise instructions for use in accordance with any of the methods described herein. The included instructions can comprise a description of administration of the aptamer to treat, delay the onset, or alleviate a target disease as those described herein. The kit may further comprise a description of selecting an individual suitable for treatment based on identifying whether that individual has the target disease. In still other embodiments, the instructions comprise a description of administering the aptamer to an individual at risk of the target disease.

The instructions relating to the use of a TNF binding aptamer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with cancer, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a TNF binding aptamer as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: TNF-Targeting Nucleic Acid Aptamers and their Theranostic Effects for Acute Lung Injury (ALI)

Materials and Methods
Chemicals and Oligonucleotides.

All chemicals were purchased from Sigma-Aldrich (St. Louis, Mo., USA) and oligonucleotides were synthesized by Integrated DNA technologies (Coralville, Iowa, USA). The sequences of aptTNF-α are 5'-GCGCCACTACAGGG-GAGCTGCCATTCGAATAGGTGGGCCGC-3' (SEQ ID NO: 1).

SELEX.

Human TNF-α-targeting aptamers were identified by nitrocellulose filter SELEX. The synthetic single-stranded DNA library was composed of 80-nucleotide-long single-stranded DNAs with 40 random sequences flanked by primer sequences, 5'-ACGCTCGGATGCCACTACAG[N]$_{40}$CTCATGGACGTGCTGGTGAC (SEQ ID NO: 2), in which N=A, T, G, C. In the first SELEX round, the $10^{15}$-molecule ssDNA library was incubated with recombinant human TNF-α proteins (R&D Systems, Minneapolis, Minn., USA). The ssDNAs that bound to TNF-α proteins were collected by nitrocellulose filter and the unbound ssDNAs were removed through repetitive washing. The TNF-α-bound ssDNAs were then eluted by heating, incubated with albumin for negative selection, and then passed through the nitrocellulose filter. The flow-through was collected and amplified by PCR. The SELEX was repeated for ten rounds. The TNF-α-bound ssDNAs and the albumin-bound ssDNAs were both subjected to next-generation sequencing (Illumina MiSeq System, Illumina, San Diego, Calif.). The output reads were clustered by FASTApatmer (Alam et al., Mol Ther Nucleic Acids. 2015; 4: e230) and subtracted with the clusters appeared in the albumin-bound group. The representative sequences that had the highest reads in the remaining clusters were then subjected to structure analysis using Mfold. Their truncated derivatives were designed according to the secondary structures predicted.

Peg Conjugation.

An excess amount of amine-labeled aptTNF-α was incubated with bifunctional N-hydroxylsuccinimide polyethylene glycol (NHS-PEG-NHS, molecular weight 20 kDa, Polysciences Inc., Warrington, Pa.) in sodium bicarbonate buffer (pH 8.3) at 37° C. for 18 h. The PEGylated dimeric aptTNF-α (aptTNF-α-PEG) were purified by non-denaturing polyacrylamide gel electrophoresis and the concentration was determined by Nanodrop spectrophotometer (Thermo Scientific, Hudson, N.H., USA).

Binding Affinity Determination.

Human TNF-α proteins (0, 8.75, 17.5, 35, 70, 140 nM, R&D Systems) were incubated with aptTNF-α (50 nM) at 37° C. for 1 h. In addition, mouse TNF-α proteins (140 nM) or BSA (140 nM) were incubated with aptTNF-α (50 nM) or aptTNF-α-PEG (50 nM) as well. The protein-bound aptamers were then collected by nitrocellulose filter and eluted by heating. The amount of the eluted aptamers was quantified by quantitative PCR (LightCycler 480 system, Roche Applied Science, Mannheim, Germany) The dissociated constant (Kd) was calculated by GraphPad Prism 5 (GraphPad Software, San Diego, Calif.), using the equation Y=Amax×X/(Kd+X). The relative amounts of protein-binding aptamers (human TNF-α proteins and mouse TNF-α proteins) were represented as fold changes, using BSA as the reference (1 fold).

Biodistribution of aptTNF-α

The mice were purchased from the National Laboratory Animal Center (Taipei, Taiwan). All the animal experiments were done according to the guidance of animal facility at Academia *Sinica*. Six-week-old Balb/c male mice were administrated with LPS (10 mg/kg, intratracheal) for the induction of ALI. IRDye® 800CW-labeled aptTNF-α (Integrated DNA technologies) was intravenously injected 1 h after LPS administration. The fluorescent signals emitted from the aptTNF-α were detected by Xenogen IVIS Imaging System 200 Series (Caliper Life Sciences, Alameda) at 2 h, 4 h, 7 h, 10 h, and 24 h post aptamer administration, respectively (Cakarova et al., Am J Respir Crit Care Med. 2009; 180: 521-32). In addition, a group of IRDye® 800CW-labeled aptTNF-α treated mice were sacrificed at 4 h post aptamer administration. Vital organs, including heart, liver, spleen, lung, kidney, and bladder, were collected and the fluorescent signal emitted from the aptTNF-α were also detected. The blood was sampled and the levels of LDH, AST, and ALT were determined by Fuji Dri-Chem 4000i (Fujifilm, Tokyo, Japan).

Cell Culture and Luciferase Activity Assays.

HEK293 cells were cultured in DMEM (Gibco BRL, Life Technologies, Grand Island, N.Y., USA) with 10% FBS (Gibco) and transfected with NF-κB reporter (pGL4.32, Promega, Madison, Wis., USA). At 24 h post transfection, cells were treated with hygromycin for the selection of antibiotic-resistant clones. The NF-κB reporter-expressing HEK293 cells were seeded into 96-well plates (2000 cells each) for overnight culture. TNF-α proteins (5 ng) along with aptTNF-α (50, 500 nM), aptTNF-α-PEG (10, 50 nM), or anti-human TNF-α antibody (10, 50 nM, R&D Systems) were added into each independent well. After 4 or 24 h incubation, the luciferase activity was determined by the luciferase assay system (Promega) following the manufacturer's protocol. Data was expressed as relative luciferase activity using the group without treatment as the negative control (0% of activity) and the group with TNF-α treatment as the positive control (100% of activity).

Acute Lung Injury (ALI) Animal Study.

For the induction of ALI, six-week-old Balb/c male mice were intratracheally treated with LPS (10 mg/kg). One hour after LPS treatment, aptTNF-α (1600 μg/kg) or aptTNF-α-PEG (32, 320 μg/kg) were intratracheally or intravenously administrated. Blood oxygen saturation was recorded at 24 h post treatment by MouseMonitor™ S plus pulse oximeter module (Indus Instruments, Webster, Tex., USA). In one study group, the mice were sacrificed. The weight of lungs was measured and tissues were subjected to RNA and protein extractions as well as immunochemistry staining. In the other, the bronchoalveolar lavage fluid (BALF) was collected. The total cell number in BALF was counted, the total protein concentration in BALF was quantified by Nanodrop spectrophotometer, and the myeloperoxidase (MPO) activity in BALF was determined by the MPO fluorometric activity assay kit (BioVision) following the manufacturer's protocol.

Quantitative PCR.

RNA was extracted from mice liver tissues by Trizol (Invitrogen) and cDNA was synthesized by SuperScript III reverse transcriptase (Invitrogen) using random hexamers (Invitrogen) according to the manufacturers' protocols. Quantitative PCR was performed on a LightCycler 480 system (Roche Applied Science, Mannheim, Germany) Primer sequences against mouse cDNA used in qPCR were listed as follows: il-1β, 5'-agttgacggaccccaaaag-3' (forward) (SEQ ID NO: 3) and 5'-agctggatgctctcatcagg-3' (reverse) (SEQ ID NO: 4); il-6, 5'-gctaccaaactggatataatcagga-3' (forward) (SEQ ID NO: 5) and 5'-ccaggtagctatggtactccagaa-3' (reverse) (SEQ ID NO: 6); cxcl2, 5'-aatcatccaaaagatact-gaacaaag-3' (forward) (SEQ ID NO: 7) and 5'-ttctctttggttcttccgttg-3' (reverse) (SEQ ID NO: 8); actb, 5'-ctaaggccaaccgtgaaaag-3' (forward) (SEQ ID NO: 9) and 5'-accagaggcatacagggaca-3' (reverse) (SEQ ID NO: 10); CCL2, 5'-catccacgtgttggctca-3' (forward) (SEQ ID NO: 11) and 5'-gatcatcttgctggtgaatgagt-3' (reverse); 5'-IL17 (SEQ ID NO: 12), 5'-cagggagagcttcatctgtgt-3' (forward) (SEQ ID NO: 13) and 5'-gctgagctttgagggatgat-3' (reverse) (SEQ ID NO: 14); IL23, 5'-tccctactaggactcagccaac-3' (forward) (SEQ ID NO: 15) and 5'-agaactcaggctgggcatc-3' (reverse) (SEQ ID NO: 16); CCND1, 5'-tttctttccagagtcatcaagtgt-3' (forward) (SEQ ID NO: 17) and 5'-tgactccagaagggcttcaa-3' (reverse) (SEQ ID NO: 18); and PCNA, 5'-ctagccatgggcgtgaac-3' (forward) (SEQ ID NO: 19) and 5'-gaatactagtgctaaggtgtctg-catt-3' (reverse) (SEQ ID NO: 20).

Western Blot and Immunohistochemistry Staining.

Primary antibodies used in the western blotting were listed as the followings: anti-GAPDH (Santa Cruz) and anti-PCNA (Cell Signaling Technology, Beverly, Mass., USA). The haematoxylin and eosin stain (H&E) was performed by pathology core at the Institute of Biomedical Sciences, Academia *Sinica*. The lung injury score was calculated according to the score system designed by the Acute Lung Injury in Animals Study Group (Matute-Bello et al., Am J Respir Cell Mol Biol. 2011; 44: 725-38). For immunohistochemistry staining, anti-Ly6G (clone 1A8, Biolegend, San Diego, Calif., USA) antibody was used at 1:100 dilution. ImmPRESS™ HRP anti-rat IgG, mouse adsorbed (peroxidase) polymer detection kit (Vectors laboratories, Burlingame, Calif., USA) was used to amplify the signal and DAB peroxidase (HRP) substrate kit (Vectors laboratories) was used for color development.

Statistics.

The results were showed as mean±standard error of mean and the P value were calculated by student t-test. The two-tailed P value lower than 0.05 was defined as statistically significant.

Results

AptTNF-α Binds to TNF-α with High Affinity and Targets TNF-α In Vivo.

Figure 2B:
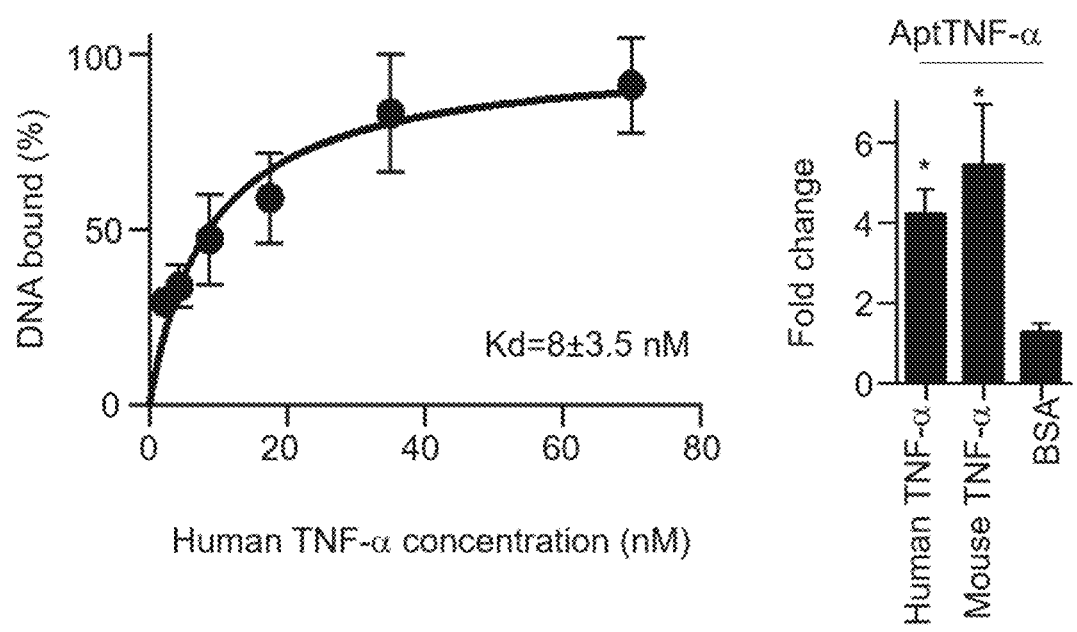

A TNF-α-targeting aptamer (aptTNF or aptTNF-α, FIG. 2A) was selected by nitrocellulose filter SELEX, analyzed by FASTAptamer, and optimized based on the predicted secondary structure using Mfold. The dissociation constant (Kd) of aptTNF-α and human TNF-α was 8 nM (FIG. 2B, left panel). As the data further showed that aptTNF-α also bound to mouse TNF-α (FIG. 2B, right panel), it was subsequently investigated in vivo binding effects of aptTNF-α using the ALI mouse model.

Figure 2C:
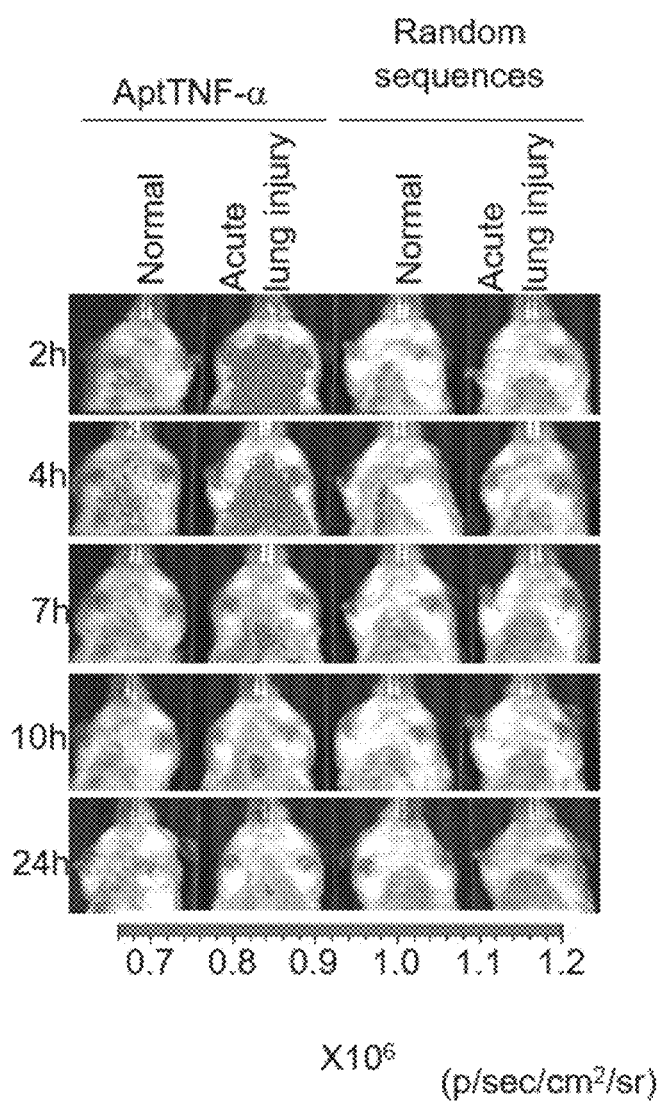
Figure 2D:
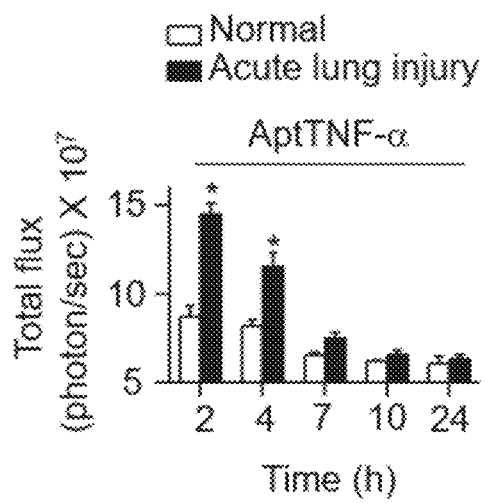
Figure 2E:
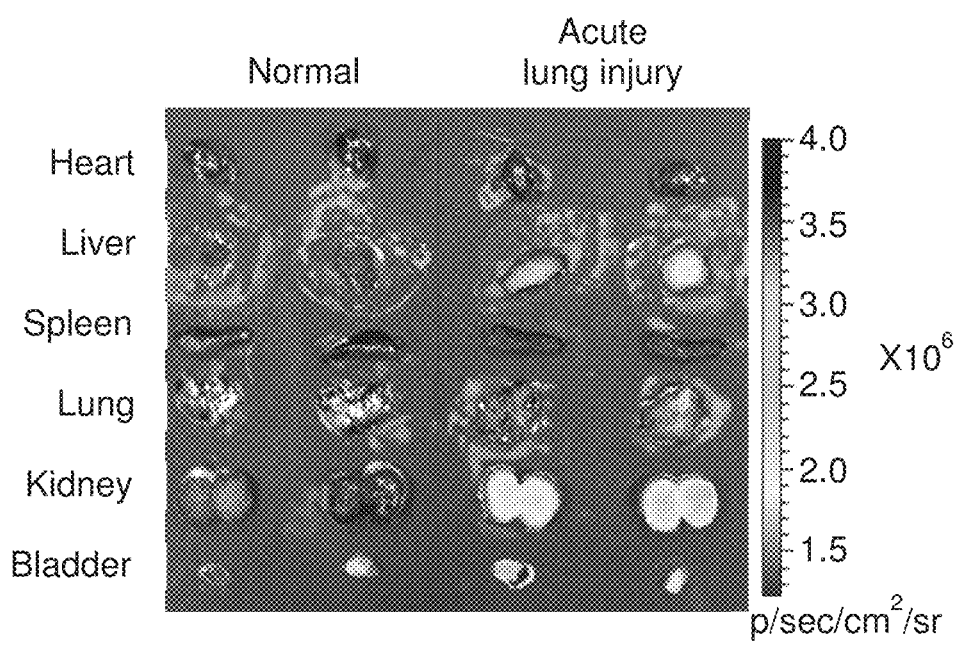
Figure 2F:
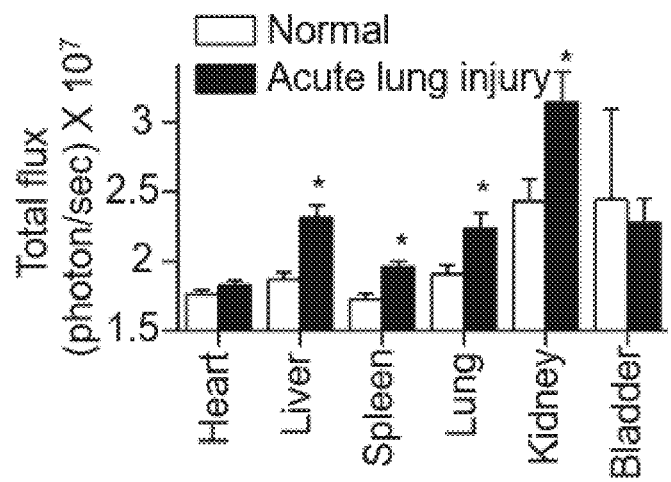
Figure 2G:
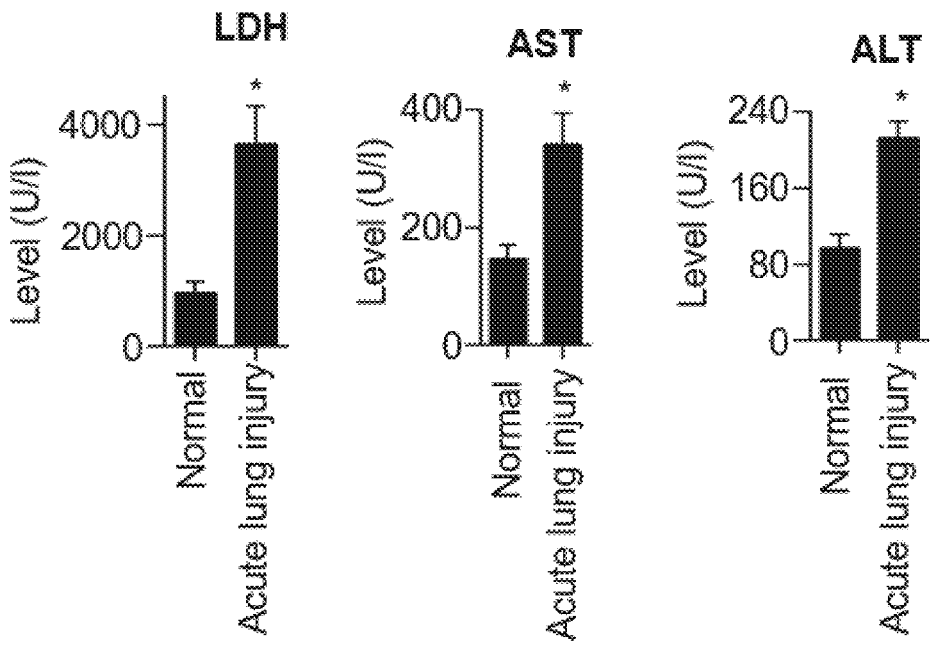

The data showed that in the ALI group, aptTNF-α signals were clearly observed in thorax at 2 h and 4 h, but disappeared at 24 h, after LPS-induced ALI (FIGS. 2C-2D). The observation was consistent with the reported TNF-α kinetics in lung tissue upon ALI (Cakarova et al., Am J Respir Crit Care Med. 2009; 180: 521-32). As SIRS can occur following ALI and lead to multiple organ damages, vital organs were collected at 4 h after the administration of aptTNF-α and examined its biodistribution. The data showed that with identical dosage of aptTNF-α administration, aptTNF-α signals were significantly increased in liver, spleen, lung, and kidney in the ALI group comparing to the control group (FIGS. 2E-2F). In the control group, aptTNF-α signals were mainly observed in kidney and bladder, the organs involved in aptamer excretion, but with a lower signal intensity than the ALI group. Further blood tests also showed that LDH, AST and ALT levels were significantly increased in the ALI group. The data supported the occurrence of end-organ damages observed in the aptTNF-α biodistribution image studies (FIG. 2G). Taken together, the data showed that aptTNF-α possesses good in vitro binding affinity toward human TNF-α and can target TNF-α in vivo as shown in the mouse ALI model.

AptTNF-α-PEG suppresses TNF-α mediated signaling

Figure 3B:
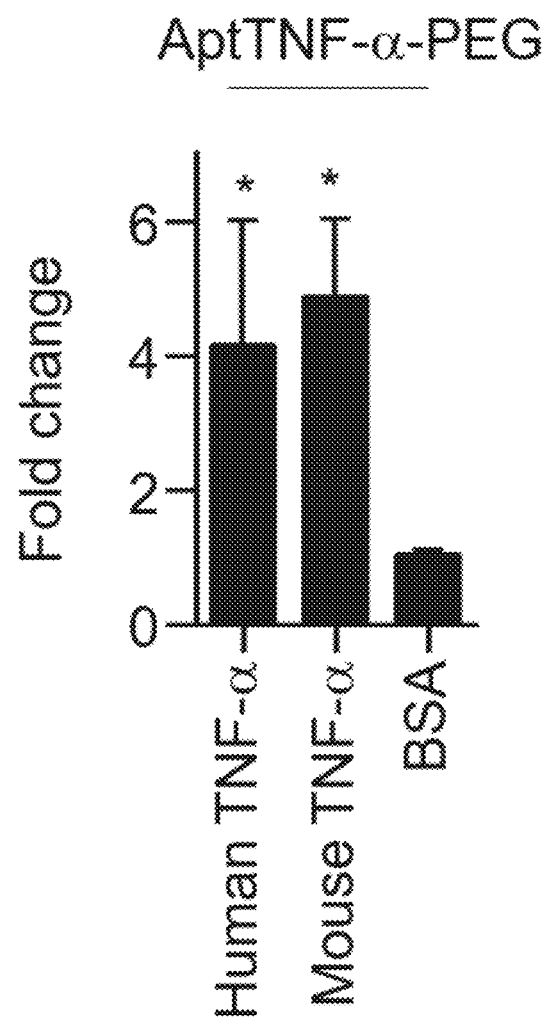

Next, it was investigated whether aptTNF-α or its derivatives efficiently inhibit TNF-α-mediated signaling. As biologically active TNF-α exists in a trimeric form in physiological conditions, synthesized dimeric aptTNF-α was synthesized by adding a polyethylene glycol (PEG) linker between two aptTNF-α monomers (aptTNF-α-PEG, FIG. 3A) to strengthen the potential antagonistic effect of aptTNF-α. The data showed that the dimeric aptTNF-α-PEG also has specific binding activity towards human and mouse TNF-α proteins (FIG. 3B).

Figure 3C:
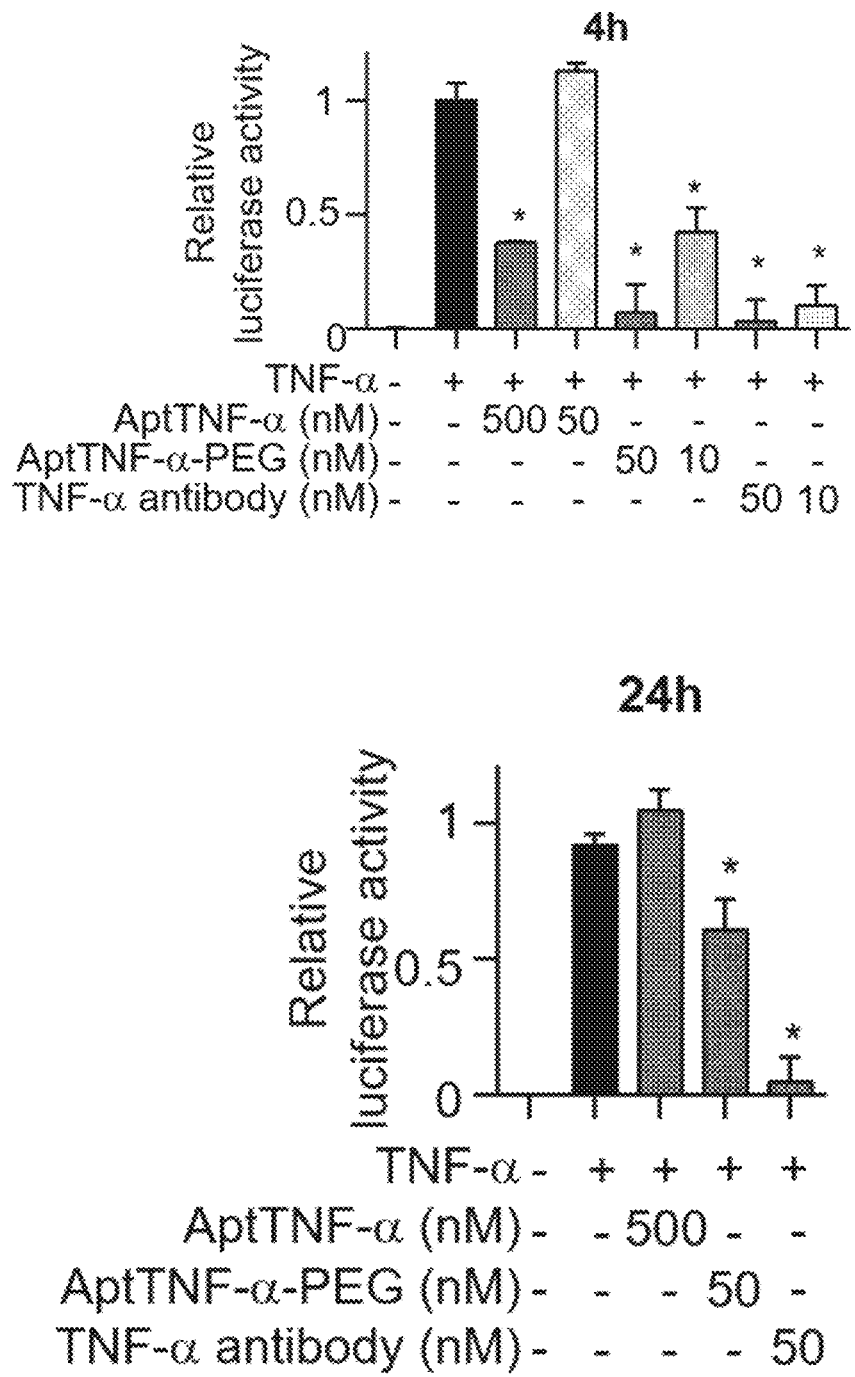

In addition, the reporter assay revealed that while the monomeric aptTNF-α effectively suppressed TNF-α/NF-κB signaling at the concentration of 500 nM, the dimeric aptTNF-α-PEG bore a better potency that inhibited TNF-α/NF-κB signaling at 50 nM as measured at 4 h after TNF-α treatment (FIG. 3C, top panel). Moreover, the suppressive effect of the monomeric aptTNF-α subsided at 24 h post TNF-α treatment and that of the dimeric aptTNF-α-PEG reduced to about 40% of the original efficacy. On the contrary, the suppressive effect of the anti-TNF-α antibody remained at 24 h post TNF-α treatment (FIG. 3C, bottom panel). These data suggested potential roles of aptTNF-α and aptTNF-α-PEG in acute illness with systemic inflammatory response as they only suppress the acute phase TNF-α signaling. This may avoid the interference of basal TNF-α signaling needed in the tissue repair phase as well as the side effects related to sustained suppression of the innate immunity.

AptTNF-α Attenuates the Severity of Acute Lung Injury

Figure 4A:
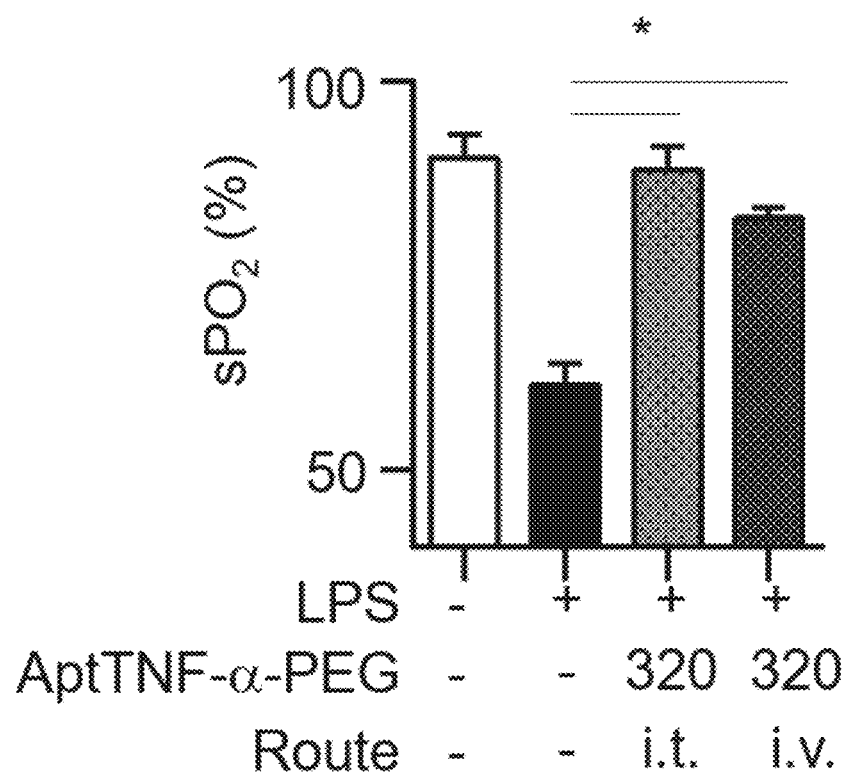
FIGS. 4A-4J include data showing that aptTNF-α and aptTNF-α-PEG suppress LPS-induced ALI through intratracheal (i.t.) or intravenous (i.v.) delivery.
Figure 4B:
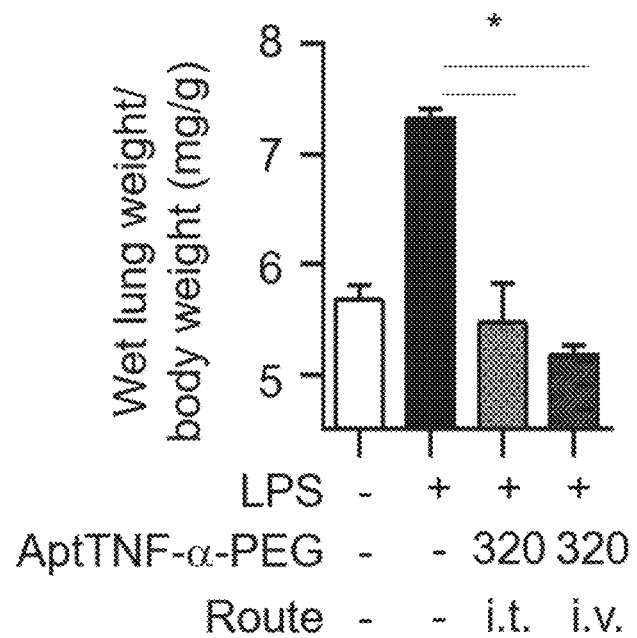
Figure 4C:
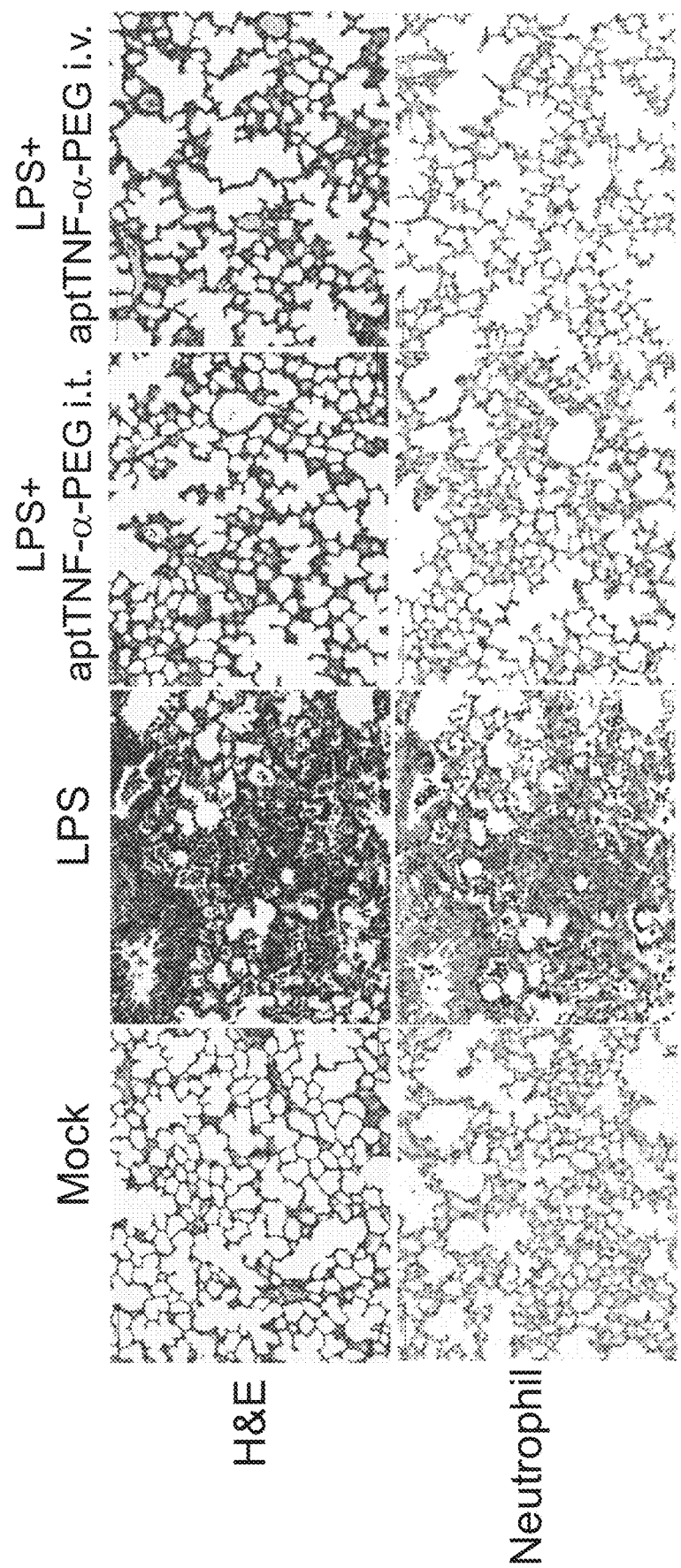
Figure 4D:
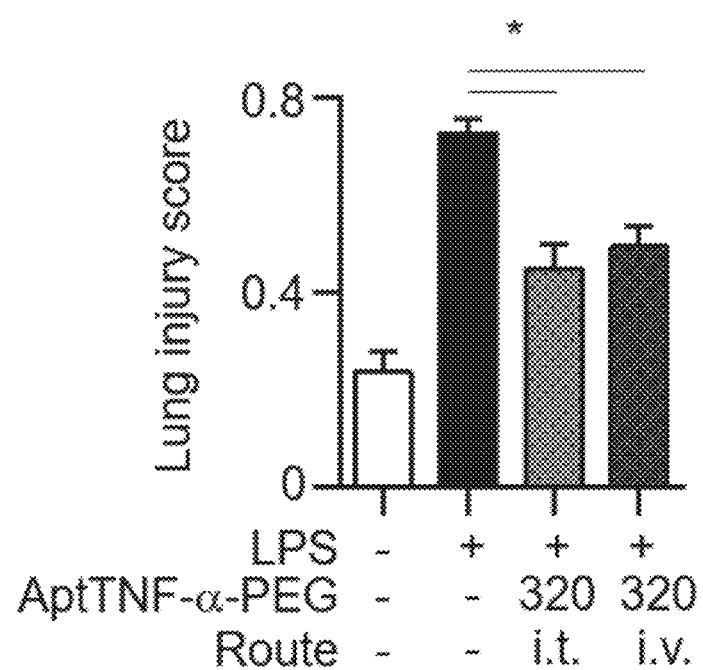
Figure 4E:
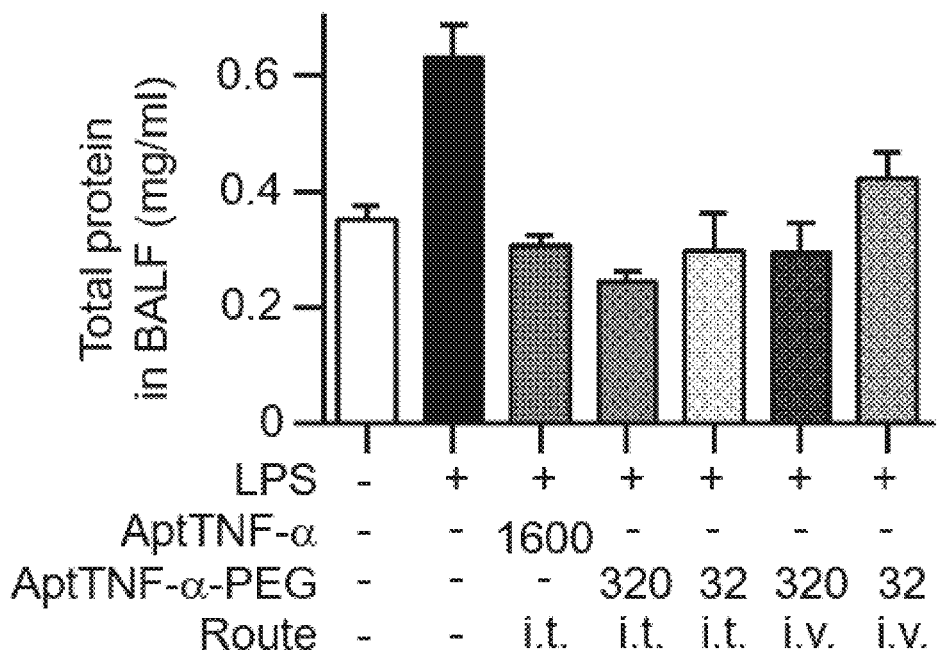
Figure 4F:
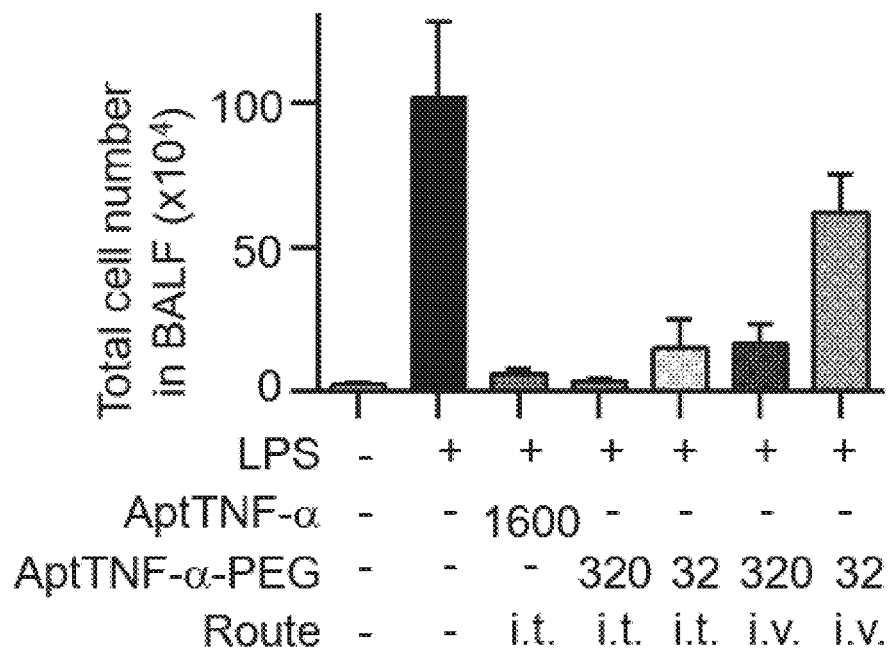
Figure 4G:
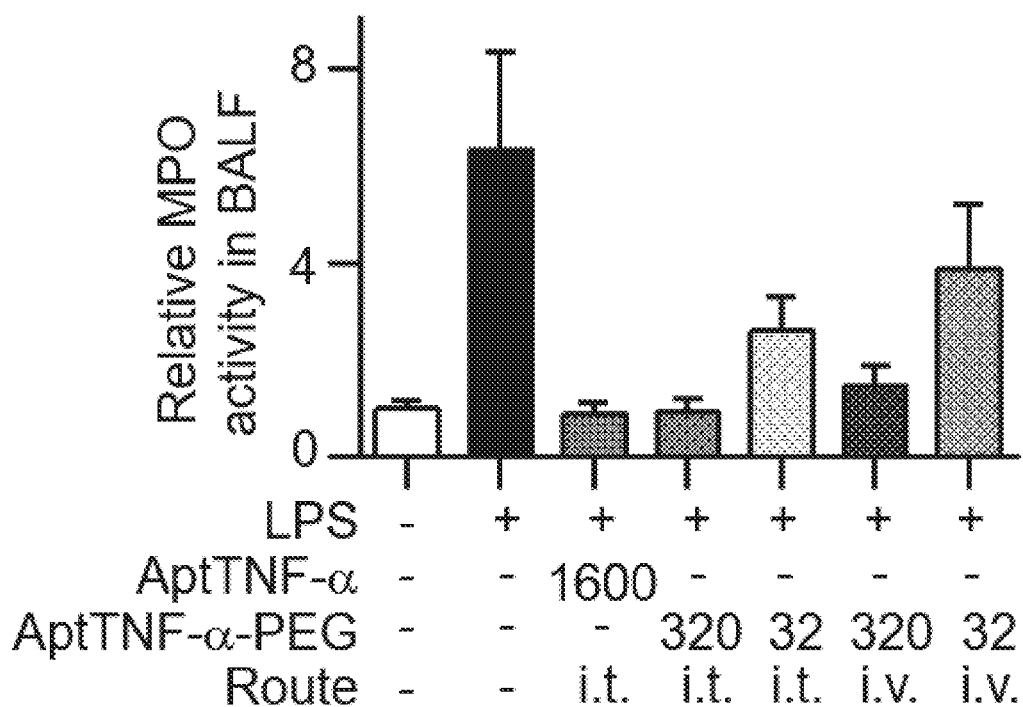
Figure 4H:
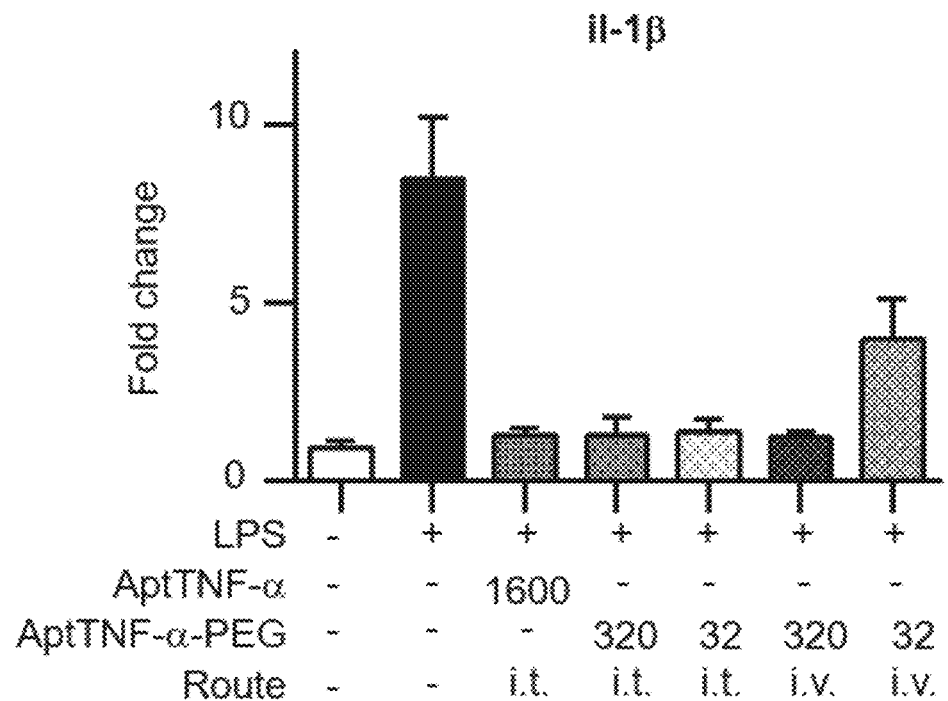
Figure 4I:
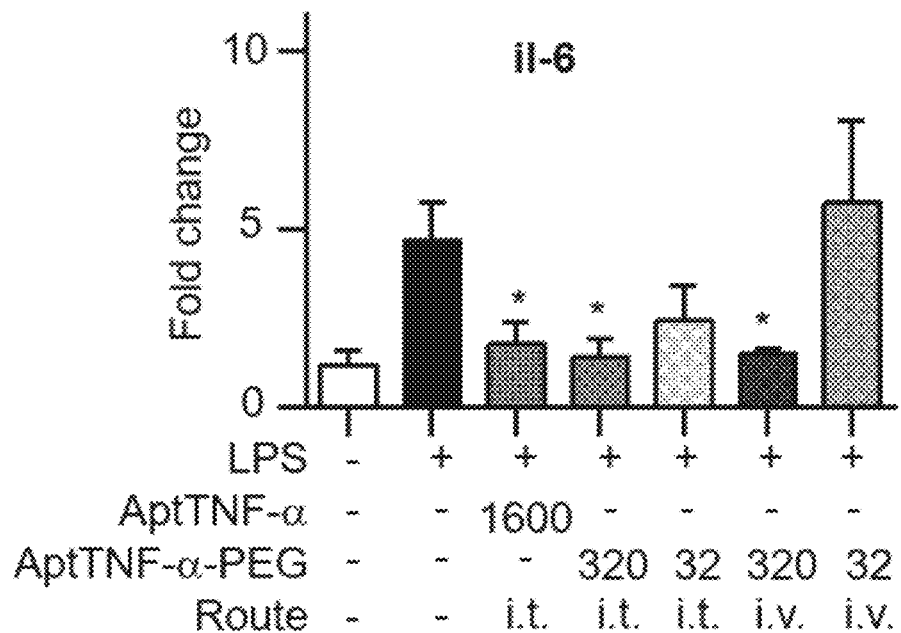
Figure 4J:
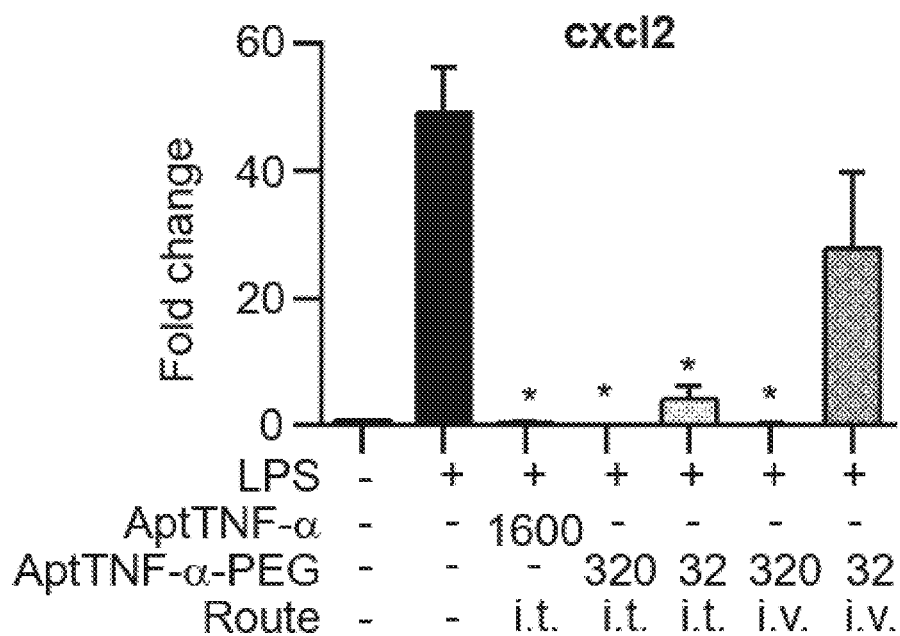

Next, the in vivo effects of aptTNF-α and aptTNF-α-PEG were investigated using the LPS-induced ALI mouse model. The data showed that LPS treatment induced respiratory distress as indicated by a significant reduction in oxygen saturation (FIG. 4A). The increased wet lung weight in the LPS-treated group suggested an enhanced permeability of the alveolar-capillary membrane upon LPS-induced injury (FIG. 4B). The histological examinations of the LPS-induced ALI group showed phenomena of alveolar septal thickening and accumulation of red blood cells, neutrophils, and fibrin strands in the alveolar spaces, and was accompanied with an increased lung injury score (FIGS. 4C-4D). Further analyses of the BALF showed increased total protein levels, total cell numbers, an enhanced myeloperoxidase (MPO) activity, and an upregulated expression of pro-inflammatory cytokines/chemokines (i1-1β, il-6, and cxcl2) (FIGS. 4E-4J). These phenotypical and molecular results fitted into the expected cascade of tissue reaction orchestrated by cytokines and chemokines in response to ALI.

Subsequently, it was shown that intratracheal or intravenous administration of aptTNF-α-PEG rescued LPS-induced injury phenotypically, histologically, and molecularly, in a dose-dependent manner (FIGS. 4A-4J). The data revealed a better efficacy of aptTNF-α-PEG when delivered via the intratracheal route, which might be related to a higher local concentration comparing to systemic delivery. Although intratracheal administration of aptTNF-α also suppressed LPS-induced ALI to some extent, this was only achieved in a relatively high drug concentration (5-fold of aptTNF-α-PEG), indicating a higher potency of aptTNF-α-PEG. Taken together, the data indicated that aptTNF-α-PEG or aptTNF-α could suppress the acute-phase apoptosis signaling mediated by the TNF-α pathway and the subsequent cytokine storm that ultimately results in tissue damage in ALI.

Example 2: Novel TNF-Targeting Aptamers with Theranostic Effects for Acute Liver Failure (ALF)

Materials and Methods

The materials methods used were the same as in Example 1 except for the animal study described below.

Acute Liver Failure (ALF) Animal Study.

To induce ALF, six-week-old Balb/c male mice were injected with D-galactosamine (D-GalN, 100 mg/kg, intraperitoneal) and human TNF-α (40 µg/kg, intravenous). Next, treatment with N-acetylcysteine (NAC, 600 mg/kg), aptTNF-α (1600 µg/kg), or aptTNF-α-PEG (3.2, 32, 320 µg/kg) was given intravenously and blood was sampled 6 h after the treatment (Saito et al., Hepatology. 2010; 51: 246-54; Sass et al., Cytokine. 2002; 19: 115-20). The blood was used for AST and ALT analyses (Fuji Dri-Chem 4000i). The mice were sacrificed 6 or 24 h after treatment. The liver tissues were collected for RNA, and protein extractions as well as immunochemistry staining.

Results

AptTNF-α Attenuates TNF-α-Mediated Acute Liver Failure (ALF) and Potentiates Early Liver Regeneration.

For ALF patients with fulminant outcomes, currently available treatment before liver transplantation is systemic infusion of N-acetylcysteine (NAC) (Bernal et al., N Engl J Med. 2013; 369: 2525-34). As ALF is TNF-α-mediated, the role of aptTNF-α and aptTNF-α-PEG in ALF was subsequently investigated and their effects were compared with NAC using the D-galactosamine (D-GalN)/TNF-α-induced mouse ALF model.

Figure 5A:
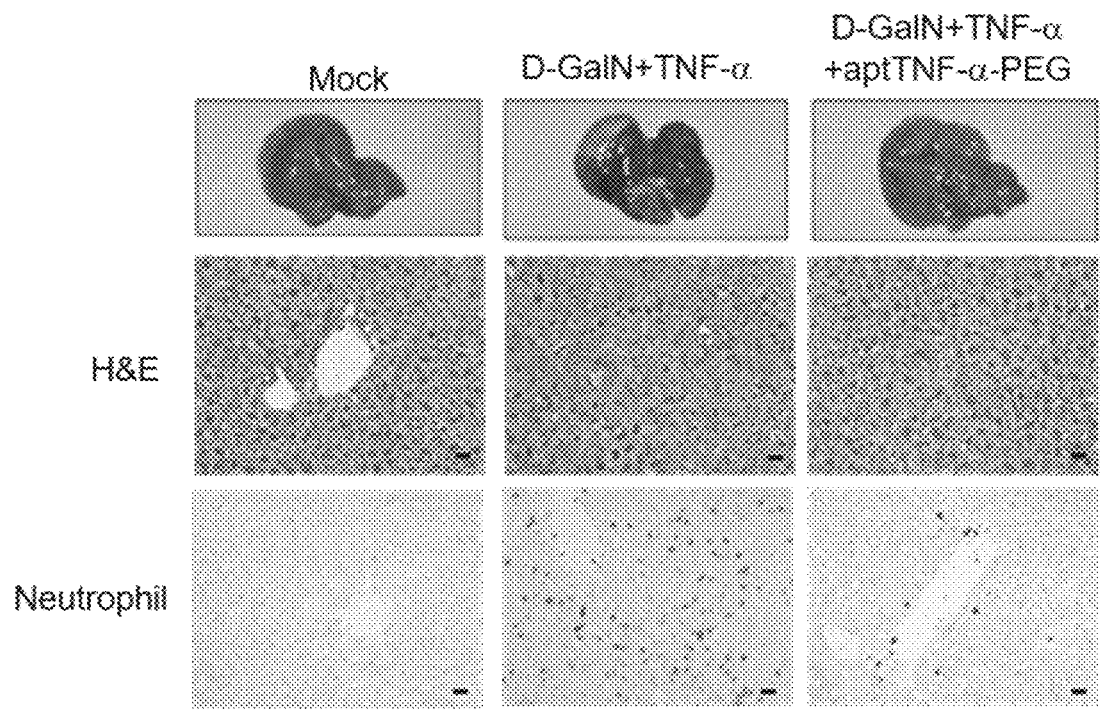
FIGS. 5A-5G include data showing that AptTNF-α and aptTNF-α-PEG attenuate the degree of D-GalN/TNF-α-induced acute liver injury and potentiate early liver regeneration.
Figure 7:
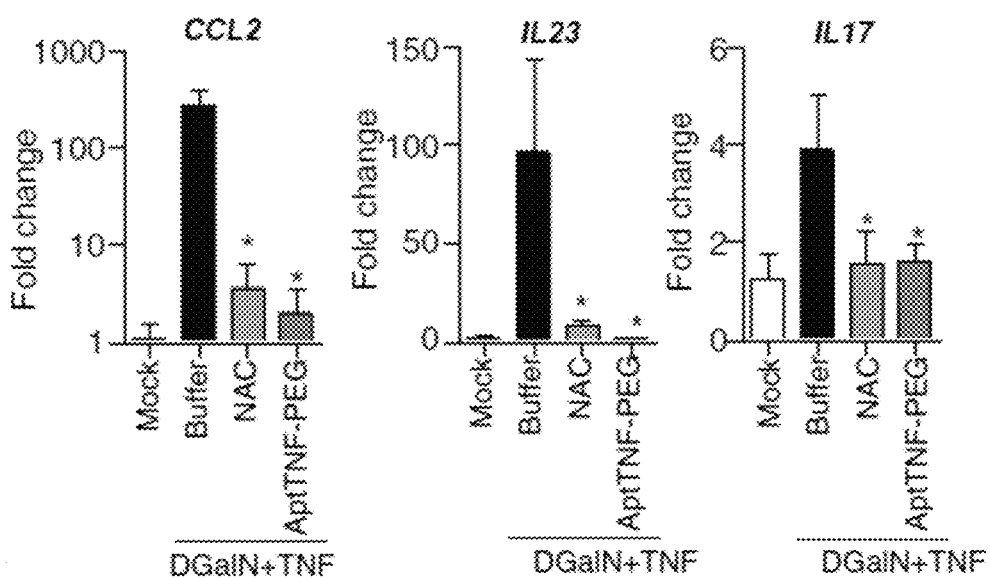
FIG. 7 is a series of charts showing that the expression level of macrophage recruitment chemokines (CCL2), and neutrophil recruitment chemokines (IL23 and IL17) were increased by TNF-α and D-GalN injection and decreased by aptTNF-α-PEG treatment.

The data showed that injection of D-GalN/TNF-α induced severe hepatocyte death accompanied with tissue hemorrhage and neutrophil infiltration. The observed liver damage was reduced with aptTNF-α-PEG treatment (FIG. 5A). Further analyses of serum AST/ALT and tissue proinflammatory cytokines/chemokine (i1-1β, il-6, and cxcl2) showed superior liver protective effects of either aptTNF-α (1600 µg/kg) or aptTNF-α-PEG (3.2 µg/kg to 320 µg/kg) to NAC (600 mg/kg) (FIGS. 5B-5F). Macrophage recruitment chemokines (CCL2), and neutrophil recruitment chemokines (IL23, IL17) were also increased by TNF and D-GalN injection and decreased by aptTNF-α-PEG treatment (FIG. 7). In addition, aptTNF-α-PEG possessed a dose-dependent liver protective effect and was again better than aptTNF-α (FIGS. 5B-5F).

Figure 5B:
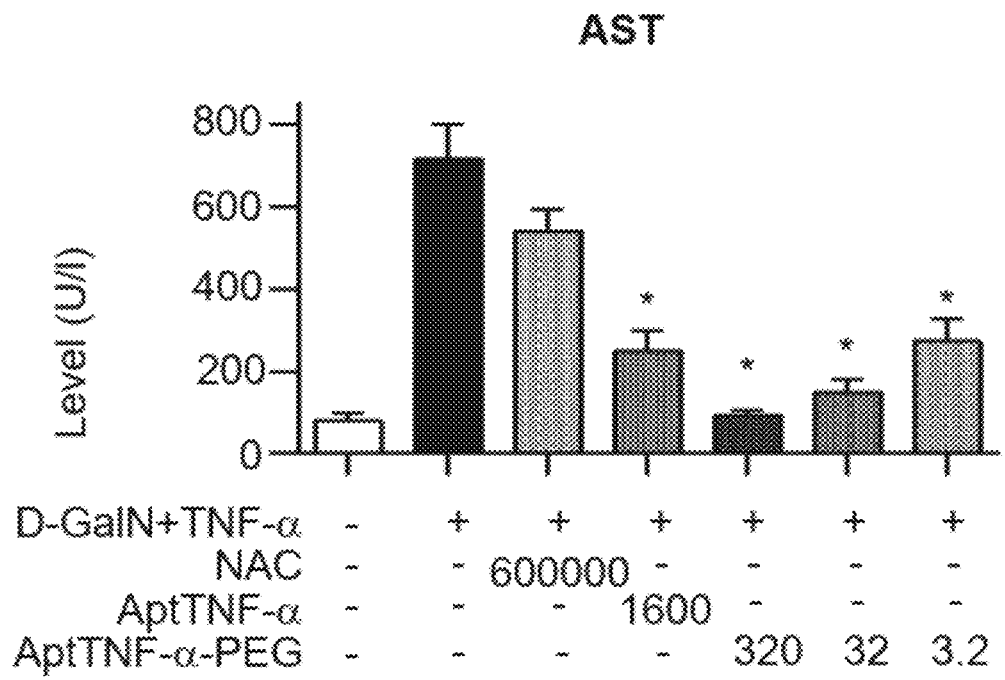
Figure 5C:
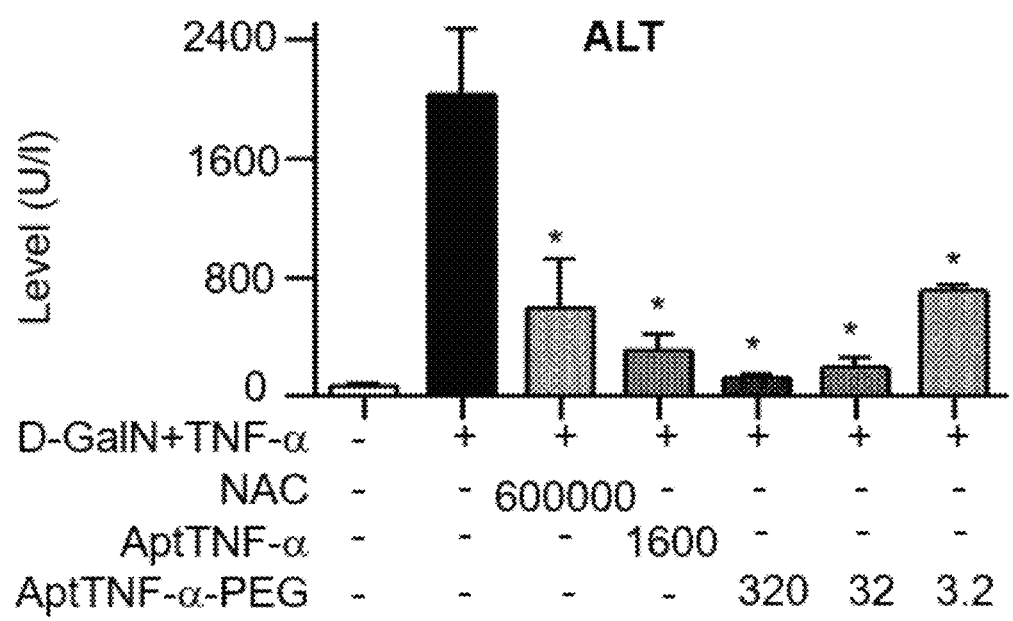
Figure 5D:
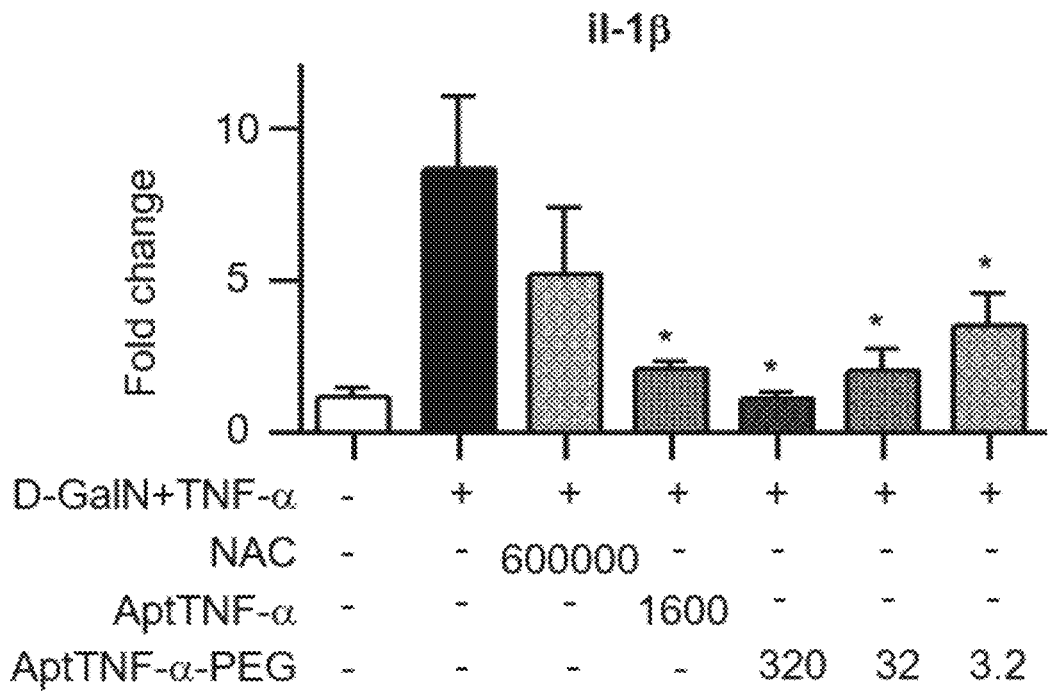
Figure 5E:
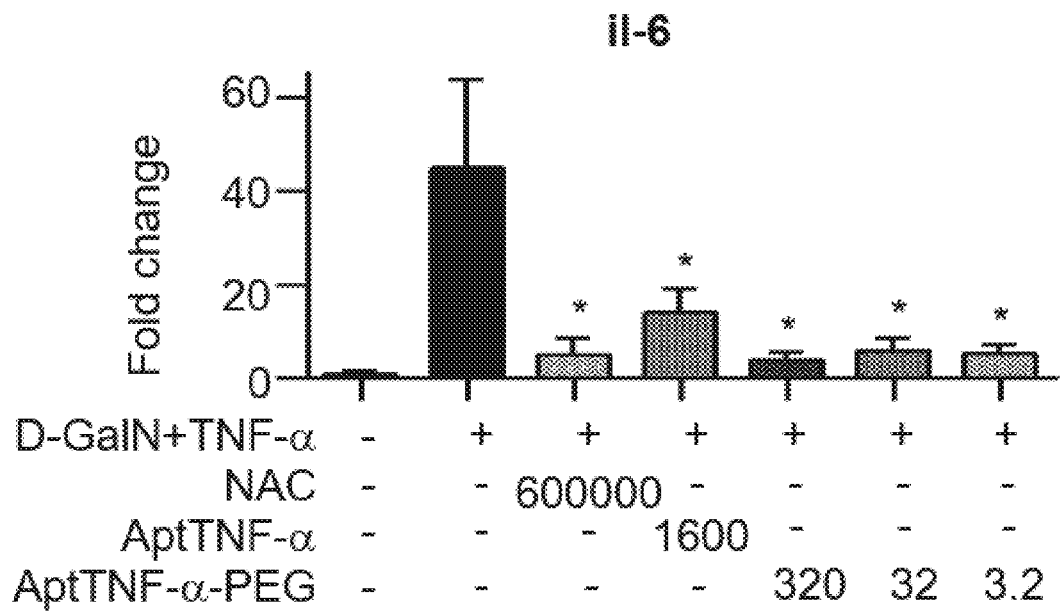
Figure 5F:
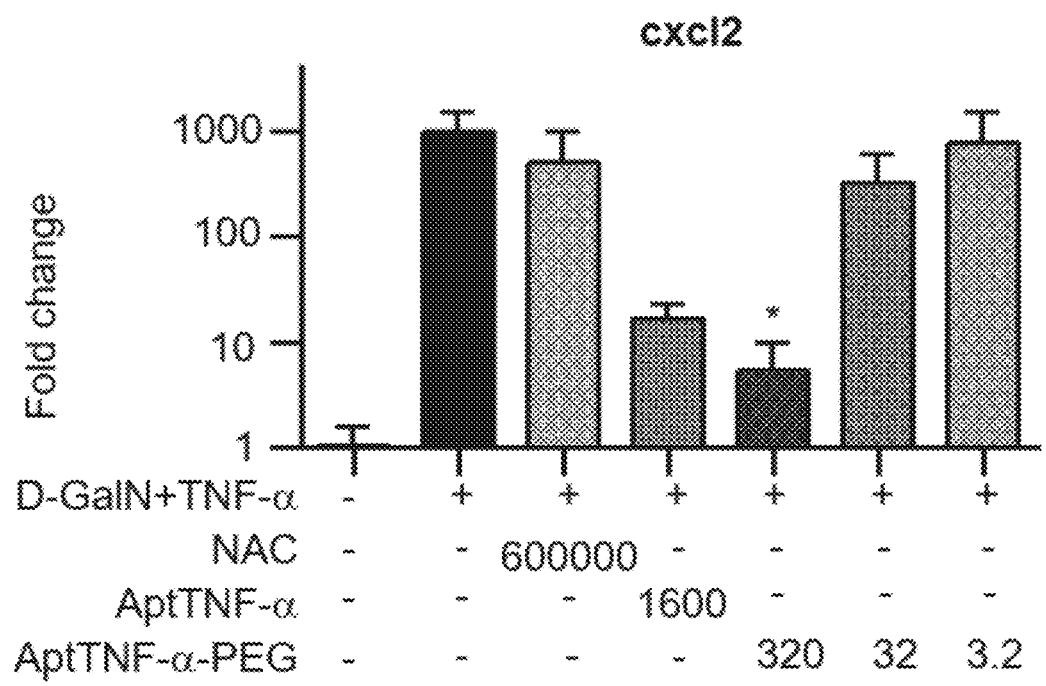
Figure 5G:
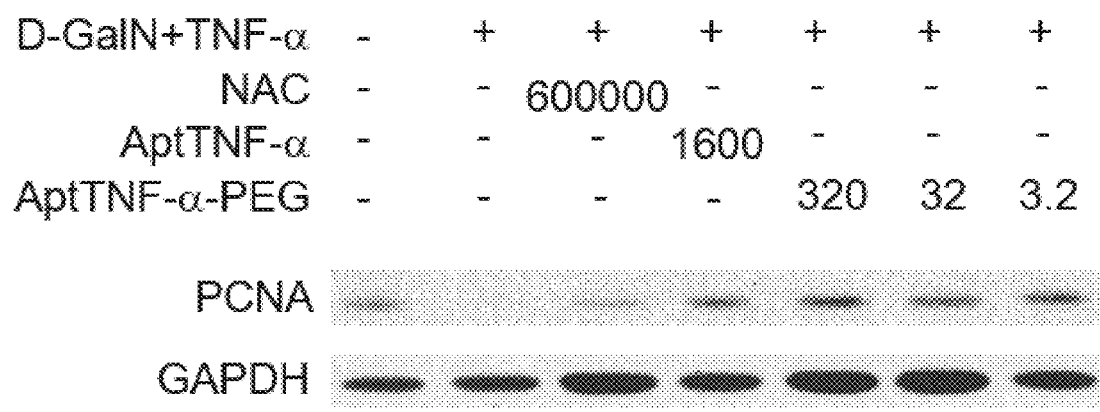
Figure 8:
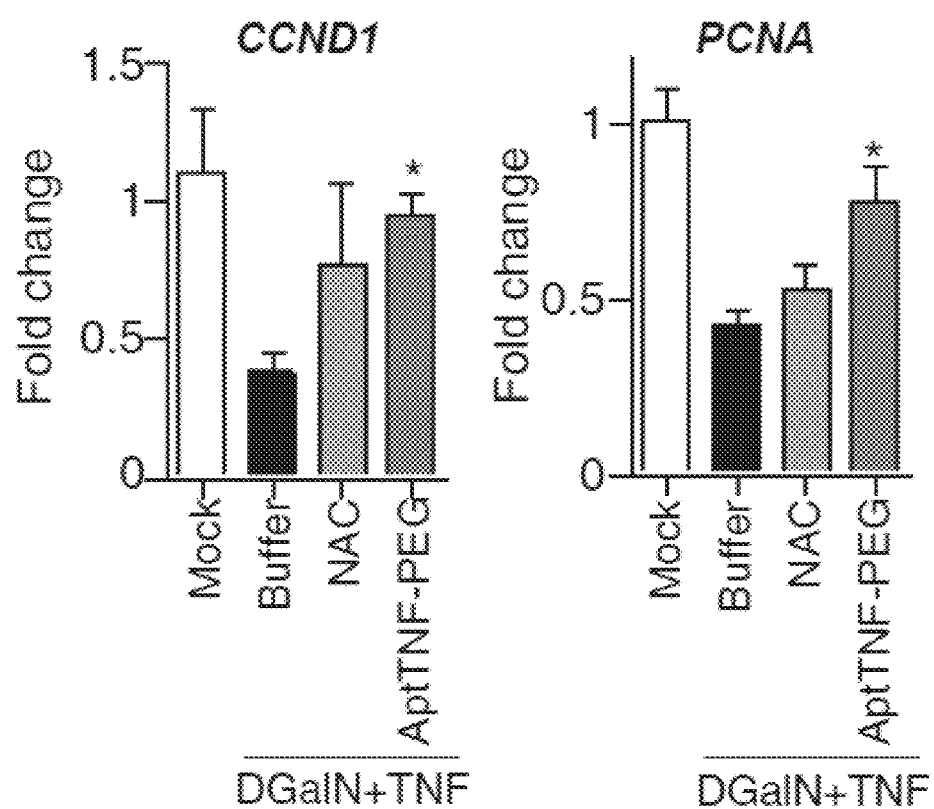
FIG. 8 is a series of charts showing that aptTNF-α and aptTNF-α-PEG treatment increased cyclin d1 (CCND1) and PCNA mRNA expression and promoted liver regeneration in a mouse model of acute liver injury.

Moreover, as hepatocytes transit from G0 to G1 phase after acute injury phase, upregulation of PCNA expression can be generally observed during liver regeneration. The data showed that both the aptTNF-α- and the aptTNF-α-PEG-treated groups had higher PCNA protein (FIG. 5G) and mRNA (FIG. 8) expression compared to the NAC-treated groups. The data suggested that hepatocytes enter G1 phase at an earlier time point in the aptTNF-α/aptTNF-α-PEG-treated group following acute injury (FIG. 5G).

The aptTNF-PEG group also revealed significantly higher cyclin D1 protein and mRNA expression (data not shown and FIG. 8), the expression in NAC group was only slightly increased (FIG. 8 and data not shown), also suggesting the hepatocytes in aptTNF-PEG group entered regeneration process at earlier time point.

Figure 6:
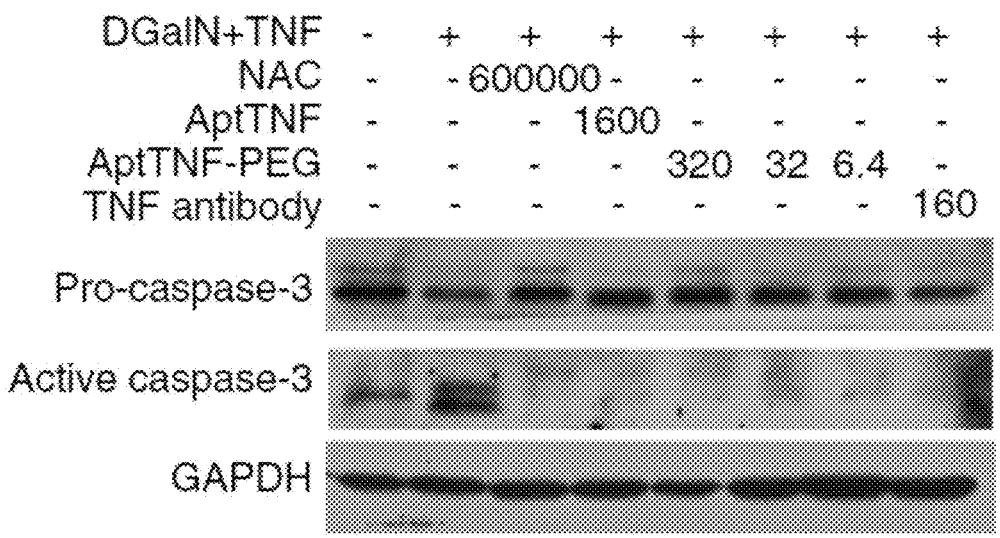
FIG. 6 is a photo showing that aptTNF-α or aptTNF-α-PEG inhibited caspase-3 activation in the liver tissue.

Furthermore, it was shown that the degree of AST and ALT elevation reversion was identical in the groups received aptTNF-α or aptTNF-α-PEG treatment. Nevertheless, while ALT elevation could be reversed in the NAC-treated group, AST remained high. (FIGS. 5B-5C). In the liver tissue, all of the treatments (including treatment using NAC, aptTNF, or aptTNF-PEG) inhibited caspase-3 activation (FIG. 6). ALT is an enzyme mainly expressed in liver. On the contrary, AST is an enzyme expressed not only in liver, but also in heart, muscle, and brain tissues. As liver failure is not merely a single organ disease but can lead to SIRS and multiple organ failures, our data suggested that treatment with aptTNF-α/aptTNF-α-PEG not only rescued acute liver damage but also suppressed the process of SIRS. The data implicate potential systemic protective effects of aptTNF-α/aptTNF-α-PEG in ALF. Taken together, the data described herein show that aptTNF-α/aptTNF-α-PEG possessed good liver protective effects and might also suppressed the process of SIRS so as to prevent multiple organ failures commonly observed in clinical practice.

Example 3: AptTNF-α Serves as a Diagnostic Agent for Monitoring TNF-α In Vivo in Liver Materials and Methods
Biodistribution Analysis For endogenous mouse TNF induction, six-week-old Balb/c male mice were intraperitoneally injected with D-GalN (650 mg/kg) and LPS (10 µg/kg) to induce acute liver failure. The mice were sacrificed 6 h after treatment and the blood serum and liver tissues were collected. For biodistribution analysis, IRDye® 800CW-labeled aptTNF (Integrated DNA technologies) were intravenously injected 0.5 h after D-GalN and LPS treatment and the fluorescent signal emitted from aptTNF were detected by Xenogen IVIS Imaging System 200 Series (Caliper Life Sciences, Alameda).

Results

AptTNF-α Serves as a Diagnostic Agent for Monitoring TNF-α In Vivo

Figure 9A:
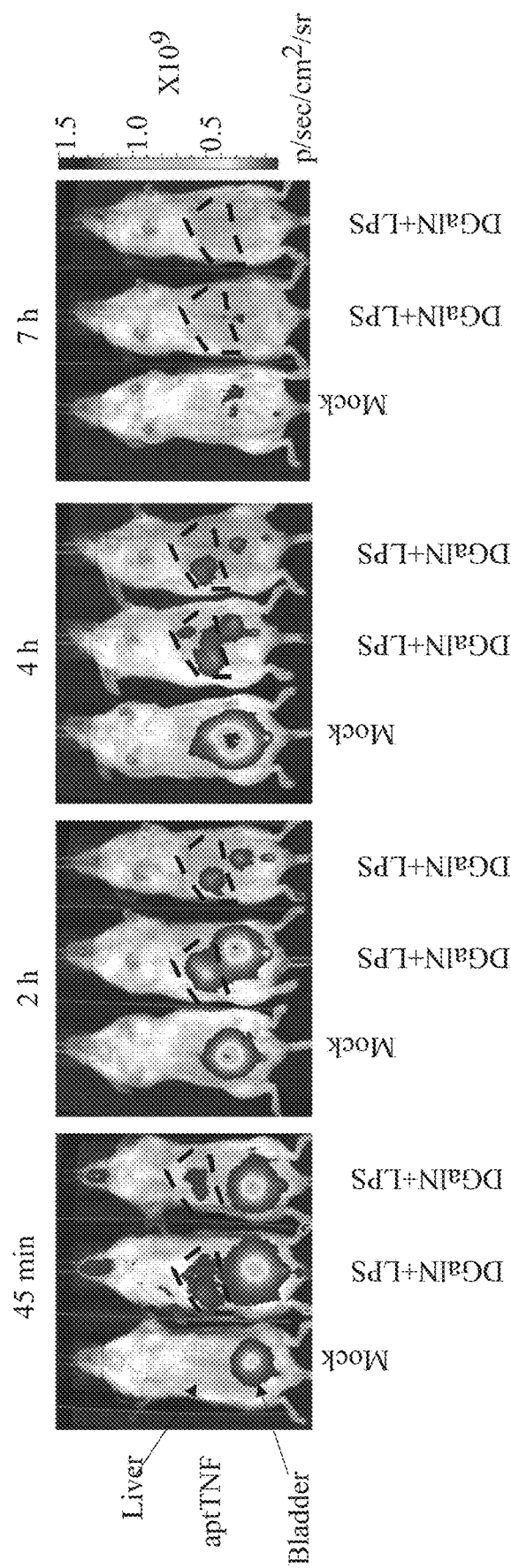
FIGS. 9A-9C include data showing that AptTNF-α can be used as a diagnostic agent for monitoring TNF-α in vivo in the liver.
Figure 9B:
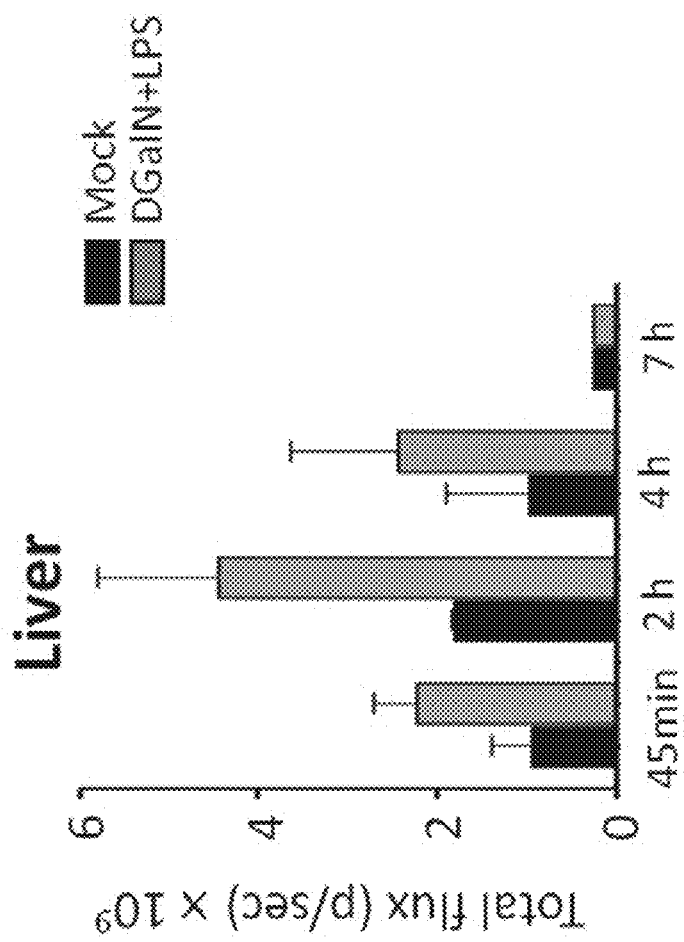
Figure 9C:
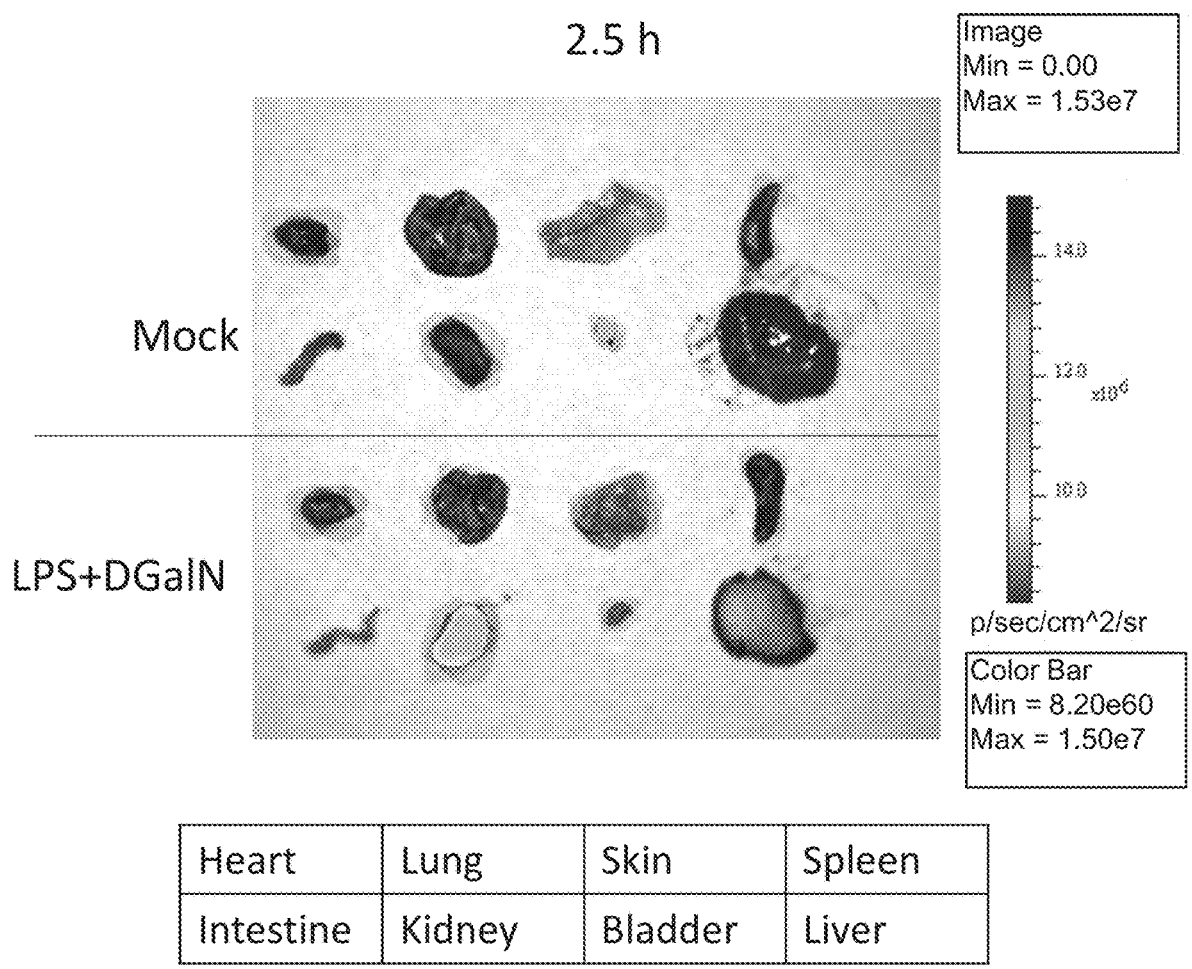

Patients who have higher TNF-α concentration in liver tissue might have better response to anti-TNF-α therapy. However, there is no routine prediction marker for TNF-α concentration or diagnostic tool to detect TNF-α in vivo. In order to reduce the unwanted side effects of anti-TNF-α therapy to non-responders, the feasibility of aptTNF-α as a diagnostic agent for monitoring TNF-α in vivo was investigated. To induce endogenous TNF-α secretion and acute liver injury in mice, LPS and D-GalN were injected into mice. Fluorescently-labeled aptTNF-α was administrated 30 min after LPS and D-GalN injection. Mice without LPS and D-GalN injection but with fluorescent-labeled aptTNF-α administration were used as negative controls. AptTNF-α significantly accumulated in liver tissues in LPS and D-GalN injection group compared to negative control group (FIGS. 9A-9C) even though a lot of aptTNF-α were excreted from kidney filtration to bladder in both groups.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A nucleic acid aptamer capable of binding human tumor necrosis factor alpha (TNFα), wherein the aptamer comprises a nucleic acid sequence that is at least 85% identical to

```
                                                (SEQ ID NO: 1)
GCGCCACTACAGGGGAGCTGCCATTCGAATAGGTGGGCCGC.
```

2. The nucleic acid aptamer of claim 1, wherein the aptamer comprises a nucleic acid sequence that is at least 90% identical to

```
                                                (SEQ ID NO: 1)
GCGCCACTACAGGGGAGCTGCCATTCGAATAGGTGGGCCGC.
```

3. The nucleic acid aptamer of claim 2, wherein the aptamer comprises a nucleic acid sequence that is at least 95% identical to

```
                                                (SEQ ID NO: 1)
GCGCCACTACAGGGGAGCTGCCATTCGAATAGGTGGGCCGC.
```

4. The nucleic acid aptamer of claim 3, wherein the aptamer comprises the nucleic acid sequence of

```
                                                (SEQ ID NO: 1)
GCGCCACTACAGGGGAGCTGCCATTCGAATAGGTGGGCCGC.
```

5. The nucleic acid aptamer of claim 1, wherein the aptamer consists of 40-100 nucleotides.

6. The nucleic acid aptamer of claim 4, wherein the aptamer consists of the nucleic acid sequence of

```
                                                (SEQ ID NO: 1)
GCGCCACTACAGGGGAGCTGCCATTCGAATAGGTGGGCCGC.
```

7. The nucleic acid aptamer of claim 1, which is conjugated to a polyethylene glycol (PEG) moiety.

8. The nucleic acid aptamer of claim 7, wherein the PEG moiety has a molecular weight of about 15-40 kDa.

9. The nucleic acid aptamer of claim 1, which is in a dimeric format containing two copies of the nucleic acid aptamer.

10. The nucleic acid aptamer of claim 9, wherein the two copies of the nucleic acid aptamer are linked by the PEG moiety.

11. The nucleic acid aptamer of claim 1, wherein the nucleic acid aptamer is conjugated to a detectable label.

12. A pharmaceutical composition, comprising the nucleic acid aptamer of claim 1 and a pharmaceutically acceptable carrier.

13. A method for inhibiting TNFα activity in a subject, the method comprising administering to a subject in need thereof an effective amount of the nucleic acid aptamer of claim 1.

14. The method of claim 13, wherein the subject is a human patient having, suspected of having, or at risk for a disease mediated by TNFα.

15. The method of claim 14, wherein the disease mediated by TNF-α is rheumatoid arthritis, psoriasis, Crohn's disease, acute liver injury, acute lung injury, acute respiratory distress syndrome, dry eye syndrome, systemic inflammatory response syndrome (SIRS)-related encephalopathy, asthma, uveitis, acute pancreatitis, acute glomerular injury, acute renal failure, ANCA-associated vasculitis, or acute encephalopathy.

16. The method of claim 13, wherein the subject has undergone or is on a therapy involving a TNFα antagonist.

17. A method for alleviating liver injury or promoting liver regeneration, comprising administering an effective amount of the nucleic acid aptamer of claim 1 to a subject in need thereof.

18. The method of claim 17, wherein the subject has liver injury associated with a liver disease.

19. The method of claim 18, wherein the liver disease is hepatitis, liver cirrhosis, liver fibrosis, fatty liver disease, liver cancer, or acute liver injury.

20. The method of claim 17, wherein the subject is at an acute phase of the disease.

21. The method of claim 13, wherein the amount of the nucleic acid aptamer is sufficient in reducing the serum aspartate transaminase (AST) level, the serum alanine transaminase (ALT) level, or both in the subject, or sufficient in reducing neutrophil infiltration into liver of the subject.

22. The method of claim 13, wherein the nucleic acid aptamer is administered intratracheally, or by inhalation or subcutaneous injection.

23. A method for detecting presence of tumor necrosis factor alpha (TNFα) in a sample, the method comprising contacting a nucleic acid aptamer of claim 11 with a biological sample suspected of containing TNFα, and examining binding of the nucleic acid aptamer to TNFα in the sample.

24. A method for monitoring tumor necrosis factor alpha (TNFα) in vivo, comprising administering to a subject in need thereof an effective amount of a nucleic acid aptamer of claim 11, and detecting localization of the nucleic acid aptamer based on a signal released by the detectable label.

25. The method of claim 24, wherein the subject is a human patient having or suspected of having a liver disease.

26. The method of claim 25, wherein the detecting step is performed by measuring the level of the signal released by the detectable label at the liver of the human patient.

27. The method of claim 17, wherein the amount of the nucleic acid aptamer is sufficient in reducing the serum aspartate transaminase (AST) level, the serum alanine transaminase (ALT) level, or both in the subject, or sufficient in reducing neutrophil infiltration into liver of the subject.

28. The method of claim 17, wherein the nucleic acid aptamer is administered intratracheally, or by inhalation or subcutaneous injection.

* * * * *

SEQUENCE LISTING

```
<160> NUMBER OF SEQ ID NOS: 20

<210> SEQ ID NO 1
<211> LENGTH: 41
<212> TYPE: DNA
<213> ORGANISM: Artificial Sequence
<220> FEATURE:
<223> OTHER INFORMATION: Synthetic polynucleotide
```

<400> SEQUENCE: 1
gcgccactac aggggagctg ccattcgaat aggtgggccg c    41

<210> SEQ ID NO 2
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(60)
<223> OTHER INFORMATION: n is a, c, g, or t

<400> SEQUENCE: 2
acgctcggat gccactacag nnnnnnnnnn nnnnnnnnnn nnnnnnnnnn nnnnnnnnnn    60
ctcatggacg tgctggtgac    80

<210> SEQ ID NO 3
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 3
agttgacgga ccccaaaag    19

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
agctggatgc tctcatcagg    20

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 5
gctaccaaac tggatataat cagga    25

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
ccaggtagct atggtactcc agaa    24

<210> SEQ ID NO 7
<211> LENGTH: 26
<212> TYPE: DNA
<213> ORGANISM: Artificial Sequence
<220> FEATURE:
<223> OTHER INFORMATION: Synthetic polynucleotide

```
<400> SEQUENCE: 7
aatcatccaa aagatactga acaaag                                          26

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
ttctctttgg ttcttccgtt g                                               21

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
ctaaggccaa ccgtgaaaag                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
accagaggca tacagggaca                                                 20

<210> SEQ ID NO 11
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 11
catccacgtg ttggctca                                                   18

<210> SEQ ID NO 12
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 12
gatcatcttg ctggtgaatg agt                                             23

<210> SEQ ID NO 13
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 13
cagggagagc ttcatctgtg t                                               21
```

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
gctgagcttt gagggatgat                                               20

<210> SEQ ID NO 15
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 15
tccctactag gactcagcca ac                                            22

<210> SEQ ID NO 16
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 16
agaactcagg ctgggcatc                                                19

<210> SEQ ID NO 17
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 17
tttctttcca gagtcatcaa gtgt                                          24

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
tgactccaga agggcttcaa                                               20

<210> SEQ ID NO 19
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 19
ctagccatgg gcgtgaac                                                 18

<210> SEQ ID NO 20
<211> LENGTH: 27
<212> TYPE: DNA
<213> ORGANISM: Artificial Sequence
<220> FEATURE:
<223> OTHER INFORMATION: Synthetic polynucleotide -continued

```
<400> SEQUENCE: 20
gaatactagt gctaaggtgt ctgcatt                                              27
```